US011426425B2

United States Patent
Kondo et al.

(10) Patent No.: US 11,426,425 B2
(45) Date of Patent: Aug. 30, 2022

(54) COMPOSITION FOR TREATING FIBROCARTILAGE TISSUE DAMAGE

(71) Applicants: Mochida Pharmaceutical Co., Ltd, Tokyo (JP); National University Corporation Hokkaido University, Sapporo (JP)

(72) Inventors: Eiji Kondo, Hokkaido (JP); Norimasa Iwasaki, Hokkaido (JP); Tomohiro Onodera, Hokkaido (JP); Wooyoung Kim, Hokkaido (JP); Yasuyuki Kawaguchi, Hokkaido (JP)

(73) Assignees: Mochida Pharmaceutical Co., Ltd., Tokyo (JP); National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 16/489,436

(22) PCT Filed: Mar. 1, 2018

(86) PCT No.: PCT/JP2018/007825
§ 371 (c)(1),
(2) Date: Aug. 28, 2019

(87) PCT Pub. No.: WO2018/159768
PCT Pub. Date: Sep. 7, 2018

(65) Prior Publication Data
US 2020/0030367 A1    Jan. 30, 2020

(30) Foreign Application Priority Data

Mar. 2, 2017 (JP) .............................. JP2017-039607

(51) Int. Cl.
*A61L 26/00* (2006.01)
*A61K 31/734* (2006.01)
*A61P 19/04* (2006.01)
*A61K 9/00* (2006.01)
*A61K 9/19* (2006.01)

(52) U.S. Cl.
CPC .......... *A61K 31/734* (2013.01); *A61K 9/0019* (2013.01); *A61K 9/19* (2013.01); *A61P 19/04* (2018.01); *A61L 26/0023* (2013.01)

(58) Field of Classification Search
CPC ... A61K 31/734; A61P 19/04; A61L 26/0023; C08L 5/04
See application file for complete search history.

(56) References Cited

U.S. PATENT DOCUMENTS 8,372,394 B2 * 2/2013 Iwasaki ................ A61K 31/734
                                                                424/93.7
2008/0119930 A1   5/2008 Osada et al.
2010/0015102 A1   1/2010 Iwasaki et al.
2014/0213524 A1   7/2014 Iwasaki et al.

FOREIGN PATENT DOCUMENTS

| JP | 4709956 B2 | 4/2011 |
|----|------------|--------|
| WO | WO 2006/013612 A1 | 2/2006 |
| WO | WO 2008/102855 A1 | 8/2008 |
| WO | WO 2011/031637 A1 | 3/2011 |
| WO | WO 2013/027854 A1 | 2/2013 |

OTHER PUBLICATIONS

Guillaume, O. et al., Journal of Biomaterials Applications, "Enhancing cell migration in shape-memory alginate-collagen composite scaffolds: In vitro and ex vivo assessment for intervertebral disc repair", 2015, vol. 29, No. 9, pp. 1230-1246 (Year: 2015).*
Igarashi, T. et al., Journal of Biomedical Materials Resarch A, "A cellular implantation system using an injectable ultra-purified alginate gel for repair of osteochondral defects in a rabbit model", 2010, vol. 94A, issue 3, pp. 844-855 (Year: 2010).*
Kobayashi et al., "Implantation of Autogenous Meniscal Fragments Wrapped With a Fascia Sheath Enhances Fibrocartilage Regeneration In Vivo in a Large Harvest Site Defect," The American Journal of Sports Medicine, 2010, 38(4):740-748.
Rey-Rico et al., "Biomedical-grade, high mannuronic acid content (BioMVM) alginate enhances the proteoglycan production of primary human meniscal fibrochondrocytes in a 3-D microenvironment," Scientific Reports, Jun. 15, 2016, 6:28170, 1-13.
Standard Textbook of Orthopedics, 12$^{th}$ Edition, Igaku-Shoin, 2015, p. 62 with partial English translation.
Zhang et al,. "Local Administration of Simvastatin Stimulates Healing of an Avascular Meniscus in a Rabbit Model of a Meniscal Defect," The American Journal of Sports Medicine, 2016, 44(7):1735-1743.
Zhang et al,. "Enhanced Meniscal Repair by Overexpression of hIGF-1 in a Full-thickness Model," Clin. Orthop. Relat. Res., 2009, 467:3165-3174.
Substantive Submission Under 37 CFR 1.114 filed Dec. 28, 2021 in U.S. Appl. No. 16/086,081.

* cited by examiner

*Primary Examiner* — Bahar Craigo
(74) *Attorney, Agent, or Firm* — Foley & Lardner LLP

(57) ABSTRACT

The present invention has an objective of providing a novel composition for treating a fibrocartilaginous tissue injury. The present invention provides a composition for treating a fibrocartilaginous tissue injury, which is to be applied to an injured fibrocartilaginous tissue part of a target and which comprises a monovalent metal salt of alginic acid, more preferably a low endotoxin monovalent metal salt of alginic acid.

20 Claims, 5 Drawing Sheets

A) Schematic view of meniscus injury model
B) Picture of meniscus injury
C) Picture of low endotoxin alginate gel

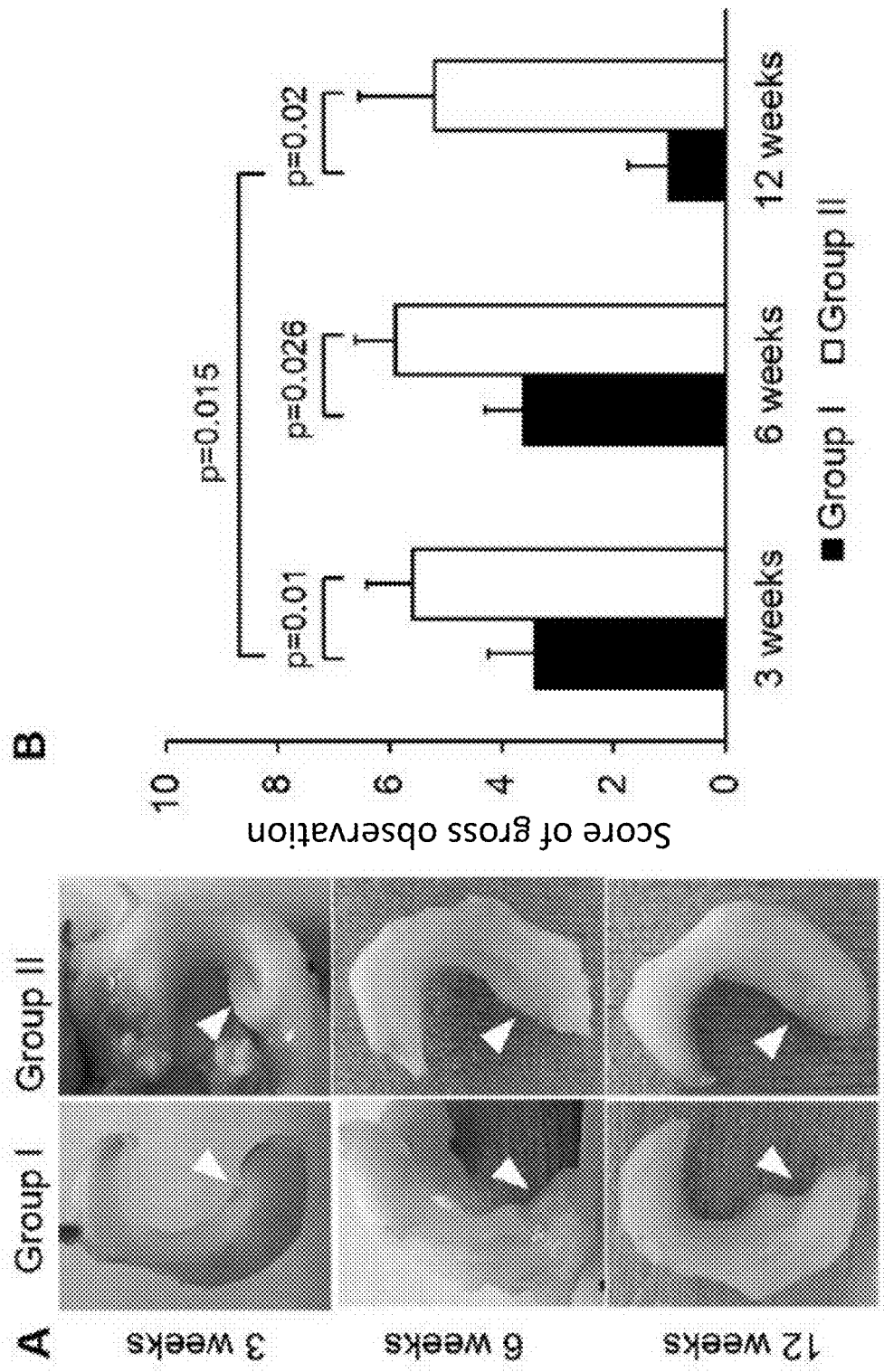
Figure 2 : Gross observation A) Pictures of menisci, B) Score of gross observation

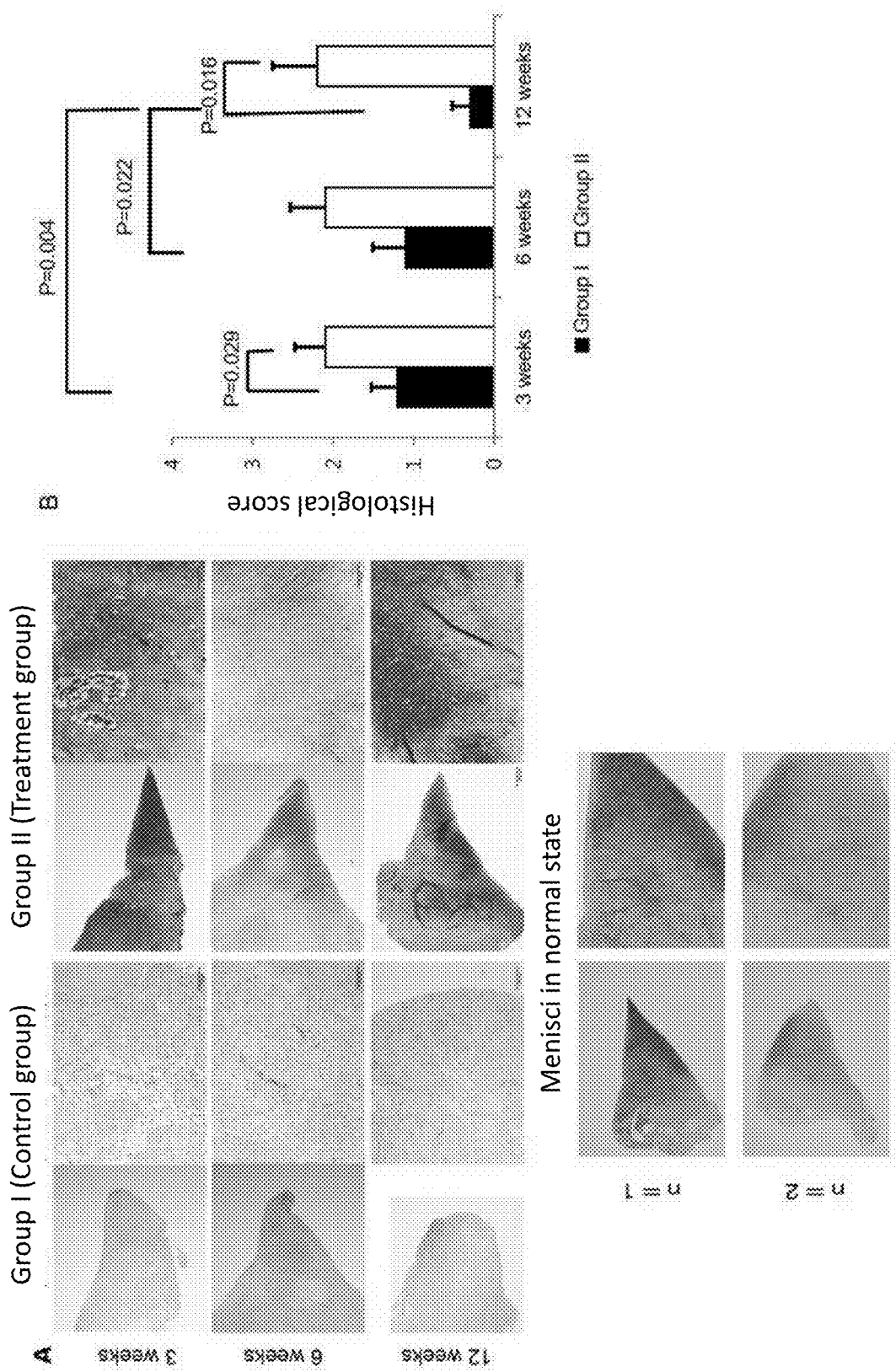
Figure 3 Histological evaluation A) Pictures after staining, B) Histological score

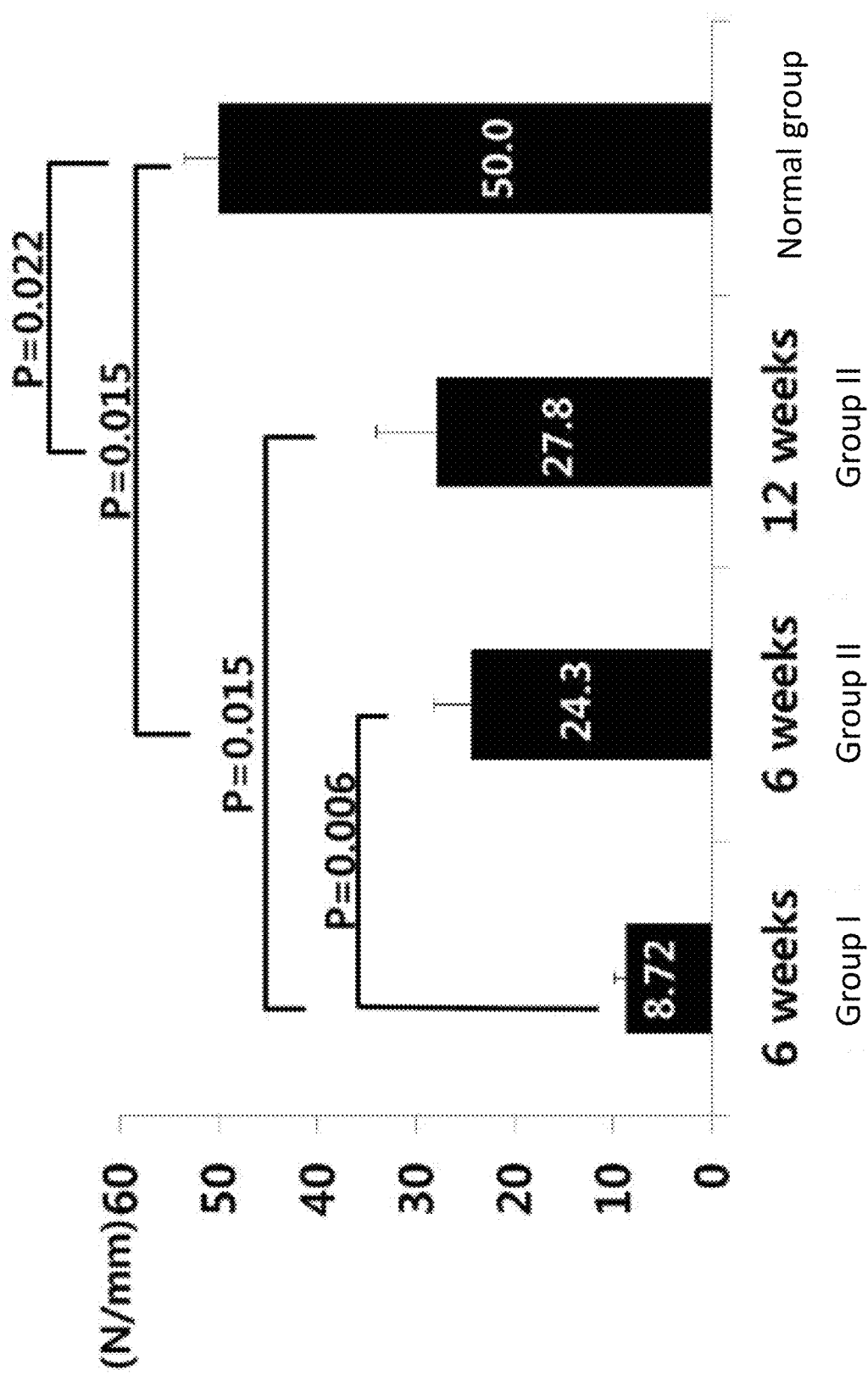
Figure 4 Results from evaluation of mechanical strength

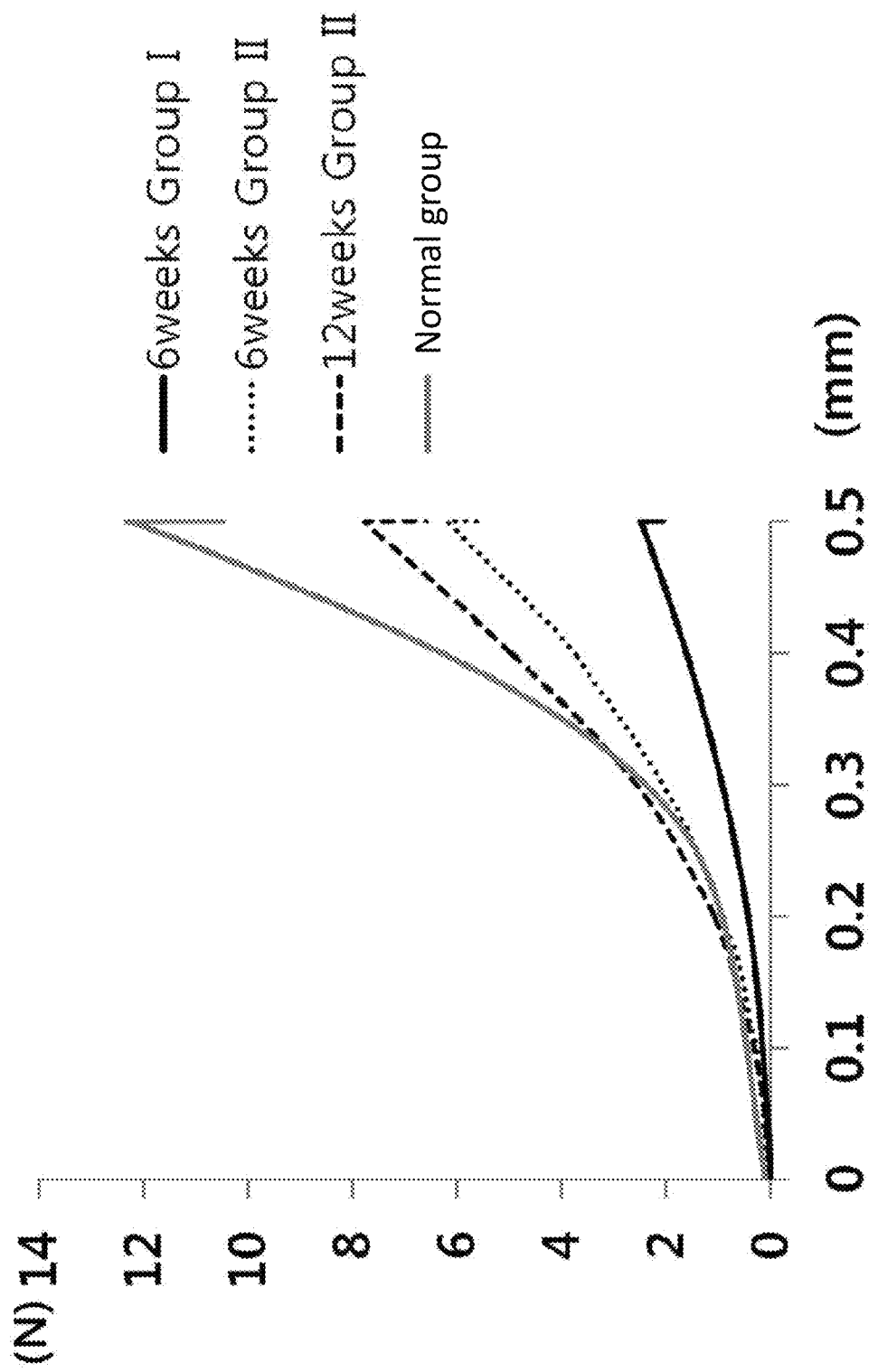
Figure 5 Results from evaluation of mechanical strength

COMPOSITION FOR TREATING FIBROCARTILAGE TISSUE DAMAGE

CROSS-REFERENCE TO RELATED APPLICATIONS

This application is the U.S. National Stage of PCT/JP2018/007825, filed Mar. 1, 2018, which claims priority to JP 2017-039607, filed Mar. 2, 2017.

TECHNICAL FIELD

The present invention relates to a composition for treating an injury of a fibrocartilaginous tissue such as a meniscus. The present invention also relates to a kit for treating a fibrocartilaginous tissue injury and to a method for treating a fibrocartilaginous tissue injury.

BACKGROUND ART

In the knee joint, the wrist joint or the like, there is tissue referred to as the meniscus or the articular disc that is arranged to make up for the space between the opposing articular cartilage surfaces. In particular, the meniscus in the knee joint is a fibrocartilage between the femur and the tibia, which is mainly a fibrous tissue. The meniscus serves as a cushion for dispersing the load of the body weight applied on the joint, stabilizes the position of the joint, smoothens the joint movement between the femur and the tibia, and protects the articular cartilage. A normal meniscus is a white and evenly translucent fibrocartilage. The meniscus mostly consists of a fibrous extracellular matrix with a mixture of small amounts of cartilage-like cells and fibrocartilage-like cells, thereby maintaining its physiological functions. While the biochemical structure of the meniscus resembles that of an articular cartilage, they greatly differ in terms of the component ratio and the component at the molecular level. In a normal meniscus in an adult knee, the moisture content accounts for 70% or more of the wet weight. The main component other than moisture is collagen, which accounts for 60-90% of the dry weight, and is slightly higher than its component ratio in the articular cartilage. 90% of the collagen is type I collagen. Meanwhile, the amount of proteoglycan is very small as compared to the articular cartilage, which is about ⅒ the proteoglycan content of the articular cartilage and only 1% of the wet weight. The meniscus differs from the articular cartilage also in terms of component in that dermatan sulfate is present as a mucopolysaccharide side chain of a proteoglycan monomer (Non-patent document 1). The menisci are either a lateral meniscus or a medial meniscus. A normal meniscus in an adult knee contains blood vessels generally only in the peripheral 10-30% of the meniscus, where nutrition is received through blood circulation. Most of other parts are nourished by the joint fluid. Since the inner circumference, an area other than the peripheral part, is an avascular area with no blood vessel, it has little self-repairing capacity. In particular, when a major meniscus injury is caused, the injured part is known to be non-healing. Moreover, since the menisci of middle-aged persons are usually degenerated, repair becomes more difficult.

The meniscus injuries may range in form, for example, including a horizontal tear, a vertical tear, a transverse tear, a bucket-handle tear, a flap tear and the like. As a method for treating such an injury, meniscus resection or meniscus suturing is often employed. While meniscus resection and suturing are generally employed methods of treatment, the chance of regeneration is limited to the vascular area in the outer circumference of the meniscus, while the self-repairing capacity is poor as described above and thus regeneration hardly takes place in the avascular area in the inner circumference of the meniscus. Furthermore, the regeneration capacity is considered to be low for a meniscus injury of an aged person since the meniscus healing capacity is generally low and the meniscus is often associated with degeneration, and thus suturing is rarely employed. In cases of a meniscus injury that developed osteoarthritis or in cases associated with locking, meniscectomy is applied since retear is highly likely to be caused even when suturing is performed. Furthermore, a torn meniscus is sometimes associated with degeneration, in which case the regeneration capacity is considered to be further low. Since the part of the meniscus will be completely lost after the resection, the cartilage in the knee joint at that site makes direct contact, where a cartilage degeneration progresses with the following 10-20 years and often leads to an articular cartilage injury. Meanwhile, the meniscus is said to be relatively regenerative in the vascular area if suturing is employed but the regenerated part is often inferior to a normal meniscus in terms of the mechanical properties, and there are many non-suturable cases, for example, in old cases or depending on the form of the tear. Moreover, even if the injured part in the avascular area of the meniscus is physically joined by suturing, the gap cannot be filled by regeneration and thus the surrounding meniscus is further injured if a load is continuously applied thereto. Accordingly, suturing is rarely employed for a tear or the like in the avascular area. In addition, aging and overuse of the joint may cause cartilage degeneration, and the wear of the joint surface at the early stage of osteoarthritis may progress to a cartilage defect over a wide area.

Therefore, since the articular menisci lack sufficient self-repairing capacity, attempts have also been made to establish methods of treatment employing cells, biotissues, biocompatible materials, or combinations thereof. Examples of such attempts include a method of treatment in which the injured meniscus part is implanted with autogenous meniscal fragments and wrapped with a fascia sheath (Non-patent document 2), a meniscus repair composition comprising about 10-50 wt % of allograft meniscus particles having an average particle size of about 10-500 μm, a carrier such as sodium hyaluronate, gelatin or alginate and a crosslinking agent (Patent document 1), and an artificial meniscus, a base material of which is a hydrogel having a network structure using an electrically charged unsaturated monomer and/or an electrically neutral unsaturated monomer (Patent document 2). In addition, there are a technique of locally applying a simvastatin-conjugated gelatin hydrogel to a rabbit meniscus defect (Non-patent document 3), a technique obtained by observing the effects of the following treatments on full-thickness meniscal defects in goats: (1) bone marrow stromal cells with the transfection of hIGF-1 gene and calcium alginate gel, (2) bone marrow stromal cells and calcium alginate gel, (3) calcium alginate gel alone, and (4) control (Non-patent document 4), and the like. In Non-patent document 4, the cell-calcium alginate gel was formed by simultaneously injecting a cell-sodium alginate solution and calcium chloride into the defects. While the detail of the calcium alginate gel used is unclear, Table 1 shows that the absorbance of the type I collagen stain, fibrochondrocytes number per unit area and a percent of cartilage-like tissue were not detected for the calcium alginate gel alone group. Non-patent document 5 describes that a defect was created in a human meniscus using a 2-mm diameter punch, and a BioMVM alginate sphere containing meniscal fibrochondrocytes was transplanted into the defect and cultured for 3 days at 37° C. and 5% $CO_2$. Such methods of treatment using cells or human tissues, however, are disadvantageous for patients from whom cells or normal tissues need to be collected and have a problem of complicated handling. Furthermore, there is yet no satisfactory technique for regenerating a meniscus to have the tissue component and the mechanical strength before the injury.

In the meantime, use of a composition containing sodium alginate has been attempted for regenerating hyaline cartilage in the injured part of the cartilage (Patent document 3).

PRIOR ART DOCUMENTS

Patent Documents

Patent document 1: WO2011/031637
Patent document 2: Japanese Patent No. 4709956
Patent document 3: WO2008/102855

Non-Patent Documents

Non-patent document 1: Standard textbook of orthopedics, 12th edition, Igaku-Shoin (2015), p. 62
Non-patent document 2: The American Journal of Sports Medicine (2010), Vol. 38, No. 4, p. 740-p. 748
Non-patent document 3: The American Journal of Sports Medicine (2016), Vol. 44, No. 7, p. 1735-1743
Non-patent document 4: Clin Orthop Relat Res (2009), 467: pp. 3165-3174
Non-patent document 5: SCIENTIFIC REPORTS 6: 28170; doi: 10.1038/srep28170, June (2016)

SUMMARY OF INVENTION

Problems to be Solved by the Invention

Under the above-described circumstances, the objective of the present invention is to provide a novel composition for treating an injury of a fibrocartilaginous tissue such as meniscus, and further to provide a kit for treating a fibrocartilaginous tissue injury and a method for treating a fibrocartilaginous tissue injury.

Another objective of the present invention is to provide a composition capable of regenerating a fibrocartilaginous tissue nearly to the component and the mechanical strength of the fibrocartilaginous tissue before the injury by a treatment of a relatively simple procedure without using cells or tissue whose acquisition and handling are complicated, and to provide a method of treatment using the same.

Means for Solving the Problems

As a method for treating a meniscus injury, the present inventors have studied the possibility of filling the injured meniscus part with a biocompatible material. Conventionally, techniques for preparing an artificial meniscus in vitro and implanting it into the joint have been studied in this therapeutic field. Since, however, the meniscus is a site consistently bearing a load, no material has been developed so far that satisfies durability and functionality. Moreover, such artificial menisci also have the problem of biocompatibility. Furthermore, conventional leading methods have been methods of treatment that employ cells or tissues. The present inventors found that regeneration of a meniscus can be promoted by applying a composition containing a low endotoxin sodium alginate to the injured meniscus part. Specifically, the results from histological evaluations, evaluations of mechanical strength and the like showed regeneration of a meniscal tissue nearly to a normal meniscal tissue. It came as a surprise in this therapeutic field to achieve remarkable regeneration effects as shown in the examples of the present invention without using cells or human tissues. The present inventors conducted further studies based on such findings and accomplished the present invention.

Thus, the present invention is as follows.

[0] A composition for treating a fibrocartilaginous tissue injury, which is to be applied to an injured fibrocartilaginous tissue part of a target and which comprises a monovalent metal salt of alginic acid.

[1] A composition for treating a fibrocartilaginous tissue injury, which is to be applied to an injured fibrocartilaginous tissue part of a target and which comprises a low endotoxin monovalent metal salt of alginic acid.

[1-1] The composition according to either one of [0]-[1], wherein the composition has fluidity or is flaky or powdery when applied to the injured fibrocartilaginous tissue part.

[2] The composition according to any one of [0]-[1-1], wherein the composition having fluidity is used so as to be at least partially cured after the application, and has fluidity upon application to the injured fibrocartilaginous tissue part.

[2-1] The composition according to any one of [1-1]-[2], wherein the timing of applying the composition to the injured fibrocartilaginous tissue part is the timing of bringing the composition into contact with the injured fibrocartilaginous tissue part.

[2-2] The composition according to any one of [0]-[2-1], wherein the composition having fluidity is used so as to be at least partially cured after the application to the fibrocartilaginous tissue.

[3] The composition according to any one of [1-1]-[2-2], wherein the composition having fluidity is cured by bringing a crosslinking agent into contact with at least a part of the surface of the composition.

[3-1] A composition for treating a fibrocartilaginous tissue injury which is to be applied to an injured fibrocartilaginous tissue part of a target, wherein the composition comprises a monovalent metal salt of alginic acid, the composition has fluidity upon making contact with the injured fibrocartilaginous tissue part of the target, and the composition is cured by bringing a crosslinking agent into contact with at least a part of the surface of the composition.

[4] The composition according to any one of [1-1]-[3] above, wherein the apparent viscosity of the composition having fluidity is 100 mPa·s-30000 mPa·s as measured with a cone-plate viscometer under a condition of 20° C.

[5-0] The composition according to any one of [0]-[4], wherein the weight-average molecular weight (absolute molecular weight) of the monovalent metal salt of alginic acid is 30,000 or more as measured by a GPC-MALS method.

[5] The composition according to any one of [1]-[4], wherein the weight-average molecular weight (absolute molecular weight) of the low endotoxin monovalent metal salt of alginic acid is 30,000 or more as measured by a GPC-MALS method.

[6-0] The composition according to any one of [1-1]-[5], wherein the concentration of the monovalent metal salt of alginic acid in the composition having fluidity is 0.1 w/w %-5 w/w %.

[6] The composition according to any one of [1-1]-[5], wherein the concentration of the low endotoxin monovalent metal salt of alginic acid in the composition having fluidity is 0.1 w/w %-5 w/w %.

[7] The composition according to any one of [1-1]-[6], wherein the composition having fluidity does not contain the crosslinking agent in an amount that allows curing of the composition before application of the composition to the injured fibrocartilaginous tissue part of the target.

[7-1] The composition according to any one of [2-1]-[6], wherein the composition having fluidity does not contain the crosslinking agent in an amount that allows curing of the composition upon making contact with the injured fibrocartilaginous tissue part of the target.

[8] The composition according to any one of [3]-[7], wherein the composition is brought into contact with the crosslinking agent after application of the composition to the injured fibrocartilaginous tissue part of the target.

[8-1] The composition according to any one of [3]-[7-1], wherein the composition is brought into contact with the crosslinking agent for curing the composition having fluidity, after application of the composition to the injured fibrocartilaginous tissue part of the target.

[9] The composition according to any one of [1-1]-[8-1], wherein the composition having fluidity has fluidity that allows injection with a 21 G needle after leaving the composition to stand at 20° C. for an hour.

[10] The composition according to any one of [0]-[9], wherein the composition is free of cells.

[11] The composition according to any one of [3]-[10], wherein the crosslinking agent is a divalent or higher valent metal ion compound.

[12] The composition according to any one of [0]-[11], wherein the injured fibrocartilaginous tissue part is occurring in at least a part of the fibrocartilaginous tissue.

[13] The composition according to any one of [0]-[12], wherein the fibrocartilaginous tissue is at least one selected from the group consisting of a meniscus, a triangular fibrocartilage, an articular disc and an annulus fibrosus of an intervertebral disc.

[14] The composition according to any one of [0]-[13], wherein the fibrocartilaginous tissue injury is at least one condition or disease selected from the group consisting of a meniscus injury, a traumatic meniscus injury, a degenerative meniscus, a discoid meniscus, osteochondritis dissecans, cartilage degeneration, an intracapsular ligament injury, a sports injury, osteoarthritis and a triangular fibrocartilage complex injury and/or degeneration.

[15] The composition according to any one of [0]-[14], wherein the injured fibrocartilaginous tissue part is a sutured injured fibrocartilaginous tissue part.

[15-1] The composition according to any one of [0]-[15], wherein the composition is applied to the injured fibrocartilaginous tissue part in combination with suturing.

[16] The composition according to any one of [0]-[15-1], wherein the composition is in a dry state or a solution state before being applied to the injured fibrocartilaginous tissue part.

[17] The composition according to [16], wherein the composition in a dry state is a lyophilizate.

[18] The composition according to any one of [0]-[17], which is used in a method for treating an injured fibrocartilaginous tissue part, the method comprising the steps of:
  (a) enabling visual recognition of the injured fibrocartilaginous tissue part through an incision or with an arthroscope or an endoscope;
  (b) if necessary, removing an unnecessary tissue from the injured fibrocartilaginous tissue part and the peripheral part thereof;
  (c) if necessary, suturing the injured fibrocartilaginous tissue part;
  (d) applying the composition containing the monovalent metal salt of alginic acid to the injured fibrocartilaginous tissue part;
  (e) if necessary, adding a crosslinking agent to the surface of the applied composition, and leaving the resultant for a predetermined period of time to bring the composition into contact with the crosslinking agent;
  (f) if necessary, washing the site where the crosslinking agent had been added; and
  (g) if necessary, closing the incision or the opening resulting from insertion of the arthroscope, the endoscope or other instrument.

[19-0] A kit for treating an injured fibrocartilaginous tissue part, comprising at least the composition according to any one of [0]-[18].

[19] A kit for treating an injured fibrocartilaginous tissue part, comprising at least the composition according to any one of [2]-[18] and a crosslinking agent.

[20-0] A method for treating a fibrocartilaginous tissue injury, comprising at least a step of applying a composition containing a monovalent metal salt of alginic acid to an injured fibrocartilaginous tissue part of a target.

[20] A method for treating an injured fibrocartilaginous tissue part, the method comprising the steps of:
  (a) enabling visual recognition of the injured fibrocartilaginous tissue part through an incision or with an arthroscope or an endoscope;
  (b) if necessary, removing an unnecessary tissue from the injured fibrocartilaginous tissue part and the peripheral part thereof;
  (c) if necessary, suturing the injured fibrocartilaginous tissue part;
  (d) applying the composition containing the monovalent metal salt of alginic acid to the injured fibrocartilaginous tissue part;
  (e) if necessary, adding a crosslinking agent to the surface of the applied composition, and leaving the resultant for a predetermined period of time to bring the composition into contact with the crosslinking agent;
  (f) if necessary, washing the site where the crosslinking agent had been added; and
  (g) if necessary, closing the incision or the opening resulting from insertion of the arthroscope, the endoscope or other instrument.

[21] A monovalent metal salt of alginic acid for use in treating a fibrocartilaginous tissue injury, wherein a composition containing the monovalent metal salt of alginic acid is applied to an injured fibrocartilaginous tissue part of a target.

[22] The composition according to any one of [0]-[21], wherein the monovalent metal salt of alginic acid is a low endotoxin monovalent metal salt of alginic acid.

Effect of Invention

The present invention provides a novel composition for treating a fibrocartilaginous tissue injury. A composition of a preferable aspect of the present invention is capable of regenerating/repairing a meniscal tissue of an injured meniscus part, especially regenerating/repairing so as to abundantly contain a fibrocartilage, and recovering the mechanical strength. In some aspects of the present invention, the composition of the present invention can be used for treating an injury of a fibrocartilaginous tissue like a meniscus with remarkable regeneration of the fibrocartilage. Moreover, this therapeutic effect is applicable to repair of a relatively large defect, and can be effective for repair of an injury in an avascular area. In addition, the present invention is capable of providing a kit for treating an injured fibrocartilaginous tissue part and a method for treating a fibrocartilaginous tissue injury.

In one preferable aspect of the present invention, the composition of the present invention can be used to prevent, treat or suppress recurrence of at least one condition or disease selected from the group consisting of a meniscus injury, a traumatic meniscus injury, a degenerative meniscus, a discoid meniscus, osteochondritis dissecans, cartilage degeneration, an intracapsular ligament injury, a sports injury, osteoarthritis and a triangular fibrocartilage complex injury and/or degeneration. Since a composition of a preferable aspect of the present invention has suitable fluidity or is flaky or powdery upon being applied to the injured part, it is capable of filling even an injured part or a torn site having a complicated shape with good adhesion without a gap between the composition and the injured part. Moreover, the composition hardly flows out from the applied/filled site even before the surface of the composition is cured with a crosslinking agent or the like, and thus it can be used even if the affected site (injured part/defective part) is not horizontal upon surgery. If necessary, the composition can be used in combination with suturing so as to promote regeneration of the injured part.

The composition of the present invention satisfies any one or more of the above-described advantages.

BRIEF DESCRIPTION OF DRAWINGS

FIG. 2 shows results from gross observation. FIG. 2A) shows pictures of menisci collected at 3, 6 and 12 weeks after the operation in Example 1, FIG. 2B) is a diagram showing scores of the extent of repair of the injured parts of the menisci collected at 3, 6 and 12 weeks after the operation.

FIG. 3 shows results from histological evaluation. FIG. 3A) shows pictures of menisci collected at 3, 6 and 12 weeks after the operation in Example 1 which have been stained with HE, safranin-O and Toluidine blue, and pictures of normal menisci which have been subjected to the same staining, and FIG. 3B) shows histological scores of the extent of repair of the injured part of the menisci collected at 3, 6 and 12 weeks after the operation.

FIG. 4 is a graph showing the results from the evaluation of mechanical strength of menisci from four groups, namely, Group I (control group) and Group II (treatment group) at 6 weeks after the operation, Group II (treatment group) at 12 weeks after the operation and the normal group (n=6), in Example 1.

FIG. 5 is a graph showing the results from the evaluation of mechanical strength of menisci from four groups, namely, Group I (control group) and Group II (treatment group) at 6 weeks after the operation, Group II (treatment group) at 12 weeks after the operation and the normal group (n=6), in Example 1.

MODES FOR CARRYING OUT THE INVENTION

Figure 1:
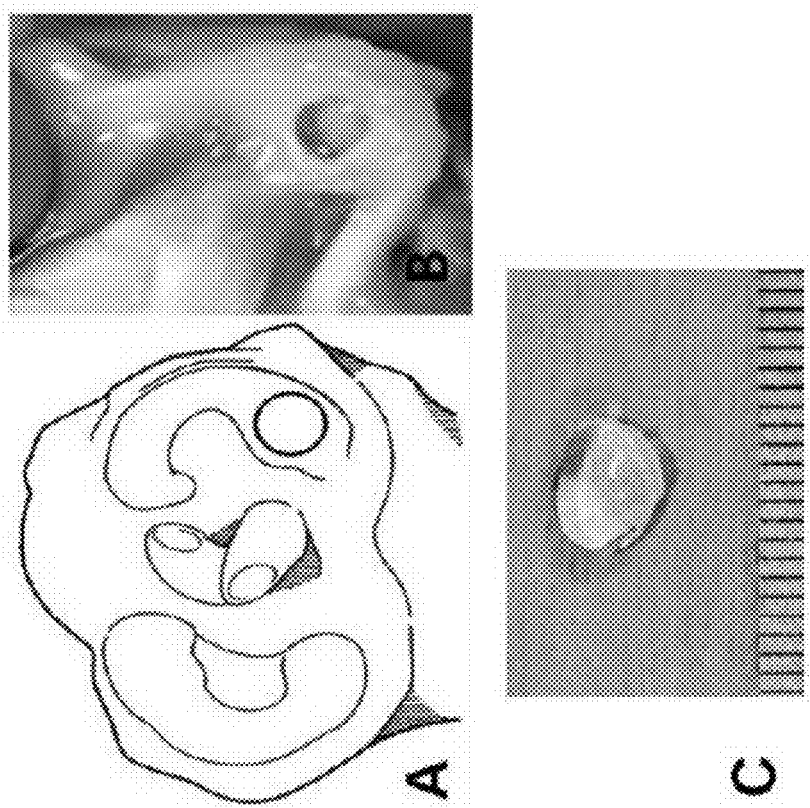
FIG. 1A) is a schematic view of a meniscus injury model, FIG. 1B) shows a picture of a meniscus injury, and FIG. 1C) shows a picture of a low endotoxin alginate gel.

Hereinafter, the present invention will be described in detail.

1. Composition of the Present Invention

The present invention relates to a composition favorably used for treating an injured part of a fibrocartilaginous tissue, more preferably an injured meniscus part.

The composition of the present invention is a composition for treating a fibrocartilaginous tissue injury, which is to be applied to an injured part of a fibrocartilaginous tissue, more preferably an injured meniscus part, of a target, and which comprises a monovalent metal salt of alginic acid (herein, sometimes referred to as a "composition of the present invention"). More preferably, the composition of the present invention is a composition for treating a fibrocartilaginous tissue injury, comprising a low endotoxin monovalent metal salt of alginic acid.

"Low endotoxin" and a "monovalent metal salt of alginic acid" are as described hereinbelow.

According to the present invention, a "fibrocartilaginous tissue" refers to a tissue that contains relatively large volume of fibrocartilage, whose examples include a meniscus, a triangular fibrocartilage, an articular disc, an annulus fibrosus of an intervertebral disc and the like.

A "meniscus" is a fibrous cartilage present in a knee joint, which is either a medial meniscus or a lateral meniscus, where it serves to disperse the pressure between the tibia and the femur and smoothens the movement of the knee joint. The meniscus can further be divided into an outer circumference and an inner circumference. Moreover, the medial meniscus can be divided into an anterior horn, an anterior segment, a middle segment, a posterior segment and a posterior horn while the lateral meniscus can be divided into an anterior segment, a middle body and a posterior segment. A meniscus is composed of a sparse number of cells, an extracellular matrix containing collagen and proteoglycan, and water, with almost no distribution of blood vessels in the inner circumference. The meniscus is characterized, for example, in that it is rich in type I collagen and type II collagen, in that it is stained with an anti-type I collagen antibody and an anti-type II collagen antibody, and in that it is stained red by safranin-O that stains proteoglycan. The meniscus may also be referred to as an "articular meniscus".

According to the present invention, a "fibrocartilaginous tissue injury" include a state where a fibrocartilaginous tissue like a meniscus is damaged due to aging, a traumatic injury or other various causes, a state where the fibrocartilaginous tissue is degenerated, or a state where the function of the tissue is deteriorated. A meniscus injury may also be observed in diseases such as osteoarthritis. According to the present invention, a site with a fibrocartilaginous tissue injury is referred to as an "injured fibrocartilaginous tissue part". For example, a site with a meniscus injury is referred to as an "injured meniscus part". In some aspects of the present invention, an injured fibrocartilaginous tissue part is occurring in at least a part of the fibrocartilaginous tissue. In some aspects of the present invention, the present invention relates to a meniscus injury treating composition for treating this injured meniscus part.

According to the present invention, a "fibrocartilaginous tissue defective part" refers to a part of an injured fibrocartilaginous tissue part where the tissue has been partially lost, and refers to the cavity of the fibrocartilaginous tissue as well as the surrounding tissue defining said cavity. In some aspects of the present invention, the method of treatment of the present invention is favorably used for treating a "fibrocartilaginous tissue defective part", especially a "meniscus defective part". According to the present invention, a "fibrocartilaginous tissue defect" is one aspect of the "fibrocartilaginous tissue injury", and a "fibrocartilaginous tissue defect" is included in the term "fibrocartilaginous tissue injury".

According to the present invention, a "fibrocartilaginous tissue injury" include diseases resulting from damage of the fibrocartilaginous tissue and/or the surrounding tissue thereof (synovial membrane, joint capsule, a submeniscus bone, etc.) due to mechanical stimulation or inflammatory response (herein, also referred to as "fibrocartilaginous tissue-related diseases"). Examples of the "fibrocartilaginous tissue-related disease" specifically include, but not limited to, a meniscus injury, a traumatic meniscus injury, a degenerative meniscus, a discoid meniscus, osteochondritis dissecans, cartilage degeneration, an intracapsular ligament injury, a sports injury, osteoarthritis and a triangular fibrocartilage complex injury and/or degeneration. In some aspects of the present invention, the method of treatment of the present invention can favorably be used especially for a meniscus-related disease among the fibrocartilaginous tissue-related diseases. Examples of the "meniscus-related disease" include, but not limited to, a meniscus injury, a traumatic meniscus injury, a degenerative meniscus and a discoid meniscus. According to the present invention, an injured part of a fibrocartilaginous tissue caused by a fibrocartilaginous tissue-related disease is one aspect of the "injured fibrocartilaginous tissue part".

A "meniscus injury" is a disease in which at least a part of the meniscus is injured due to a traumatic injury or a meniscus degeneration. Herein an "injury" includes a "defect" and a "tear". A "tear" includes various forms of tear including a "horizontal tear", a "vertical tear" a "transverse tear" and a "degenerate tear".

A "traumatic meniscus injury" is one of the "meniscus injuries" and is a disease in which at least a part of the meniscus is injured due to external impact such as contact and an accident in sports.

A "degenerative meniscus" refers to a disease where the number of meniscus cells, the moisture content, the extracellular matrix (type I and II collagen, aggrecan, etc.) and the like are decreased due to aging or the like to cause morphological changes and functional disorders, which may progress such that the meniscus can no longer serve as a shock absorber.

While a meniscus usually has a crescent shape, a "discoid meniscus" refers to a congenitally half-moon-shaped meniscus, where the meniscus is interposed between the cartilages. Herein, a "discoid meniscus" also includes a meniscus injury and symptoms like pain and locking associated with the discoid meniscus.

"Osteochondritis dissecans" is a disorder in which a cartilage become loose within a joint, which is sometimes associated with a discoid meniscus.

"Cartilage degeneration" is a disease that causes degeneration of the cartilage due to aging or the like.

An "intracapsular ligament injury" refers to a disease in which the ligament is injured when a large force is applied to the joint upon a sports injury, accident or the like, depending on the direction of the external force.

A "sports injury" is a disease in which the tissue is injured when a large abrupt force is applied to the body upon a tumble, collision or the like during an activity such as sports.

"Osteoarthritis" is a degenerative disease in which the articular cartilage wears away due to aging and overuse of the joint, which is sometimes caused by a meniscus injury or the like.

A "triangular fibrocartilage complex injury and/or degeneration" is an injury and/or degeneration of a soft tissue present on the little finger side (between the ulna and the carpal bones) of the wrist joint (wrist). A triangular fibrocartilage complex (TFCC) consists of the articular disc and some ligaments.

Fibrocartilaginous tissue injuries may be classified by grades according to the degree of the conditions and the lesion of the injured parts. As to the classification by staging, the terms grade and stage are used herein synonymously.

An "avascular area" refers to an area of a fibrocartilaginous tissue with almost no distribution of blood vessels. While blood vessels are distributed in the outer circumferences of the medial and lateral menisci, the inner circumferences of the menisci are avascular areas where the self-repairing capacity and the tissue regeneration are considered to be poor. In one aspect of the present invention, the composition of the present invention is favorably used for a meniscus injury caused in an avascular area of the meniscus.

A "target" refers to a human or an organism other than a human, for example, a bird or a non-human mammal (for example, bovine, monkey, cat, mouse, rat, guinea pig, hamster, pig, dog, rabbit, sheep and horse).

"Application" means to fill an injured fibrocartilaginous tissue part with a composition of the present invention in an amount sufficient to embed a degenerated portion, a shrunken portion, a removed portion, a defective part or the like of the injured part of the fibrocartilaginous tissue.

The phrase "at least partially cured" will be described hereinbelow.

The phrase "to contain a monovalent metal salt of alginic acid" means that the composition of the present invention contains a monovalent metal salt of alginic acid in an amount sufficient to regenerate the fibrocartilaginous tissue injury applied with the composition. In addition, the phrase "to contain a low endotoxin monovalent metal salt of alginic acid" means that the composition of the present invention contains a low endotoxin monovalent metal salt of alginic acid in an amount sufficient to regenerate the fibrocartilaginous tissue injury applied with the composition.

The phrase "to have fluidity" will be described in "8. Application of composition of the present invention" below.

The composition of the present invention may be provided in a solution state using a solvent, in a dry state as a lyophilizate (particularly, lyophilized powder) or the like, or in a flaky or powdery state. If the composition of the present invention is provided as a lyophilizate, it may be used in a state having fluidity (e.g., in a solution state) by using a solvent upon application. The solvent is not particularly limited as long as it can be applied to an organism, and it may be, for example, injectable water, purified water, distilled water, ion exchanged water (or deionized water), Milli-Q water, physiological saline and phosphate buffered physiological saline (PBS). Preferably, it is injectable water, distilled water, physiological saline or the like that can be used for treating a human or an animal.

The composition of the present invention is applied to an injured fibrocartilaginous tissue part in a solution state so that it can fill inside the injured part with good adhesion. If the injured part is to be sutured, the composition can be applied to the sutured injured part in a solution state so as to fill the gap at the sutured site or to efficiently solidify the surface. The composition of the present invention can be applied in a solution state so that it is expected to promote repair of the sutured tissue at a torn site upon repair surgery of the meniscus, and to prevent re-injury due to a load, exercise or the like. Furthermore, if the composition of the present invention is to be applied in a solution state (including a sol state), it can be arthroscopically injected in a sol state into an articular cavity and can exert the function as a material for filling an injured part of the fibrocartilaginous tissue such as a meniscus while maintaining suitable viscosity, adhesion and elasticity. Thus, the composition of a preferable aspect of the present invention has fluidity upon application to an injured fibrocartilaginous tissue part, more specifically, upon making contact with an injured fibrocartilaginous tissue part. Herein, the phrase "to have fluidity upon making contact with an injured fibrocartilaginous tissue part" means that the composition of the present invention has fluidity when the composition first makes contact with the injured part for filling the injured fibrocartilaginous tissue part. Therefore, this does not include a case where the composition lacks fluidity upon making contact with the injured part, for example, a case where the composition of the present invention and a crosslinking agent are injected into the injured part at the same time. In some aspects of the present invention, since the composition of the present invention is capable of repairing a meniscus without using cells as will be described below, it can be used conveniently at a clinical site. Furthermore, the composition of the present invention can also be used in combination with a usual surgical procedure or other method of treatment for meniscus injuries.

A powdery or flaky composition of the present invention may be applied to an injured fibrocartilaginous tissue part with a spray or the like. Since a powdery or flaky composition has good adhesiveness to an injured part, it is advantageous in that it can be handled easily and, similar to the composition in a solution state, it can be applied easily to an injured part such as a torn site.

2. Monovalent Metal Salt of Alginic Acid

The "monovalent metal salt of alginic acid" is a water-soluble salt formed by ion exchange between a hydrogen atom of carboxylic acid at position 6 of alginic acid and a monovalent metal ion such as $Na^+$ or $K^+$. While specific examples of the monovalent metal salt of alginic acid include sodium alginate and potassium alginate, sodium alginate which is commercially available is particularly preferable. A solution of monovalent metal salt of alginic acid forms a gel when mixed with a crosslinking agent.

The "alginic acid" used in the present invention is a biodegradable, high molecular weight polysaccharide that is a polymer obtained by linearly polymerizing two types of uronic acids in the forms of D-mannuronic acid (M) and L-guluronic acid (G). More specifically, the alginic acid is a block copolymer in which a homopolymer fraction of D-mannuronic acid (MM fraction), a homopolymer fraction of L-guluronic acid (GG fraction) and a fraction in which D-mannuronic acid and L-guluronic acid are randomly arranged (MG fraction) are linked arbitrarily. The composite ratio of the D-mannuronic acid to the L-guluronic acid (M/G ratio) of the alginic acid varies according to the type of the organism serving as the origin thereof (mainly algae), is affected by the habitat of that organism and the season, and varies over a wide range from a high G type having an M/G ratio of about 0.1 to a high M type having an M/G ratio of about 5.

While a monovalent metal salt of alginic acid is a high molecular weight polysaccharide and it is difficult to accurately determine the molecular weight thereof, it has a weight-average molecular weight generally in a range of 10,000-10,000,000, preferably 20,000-8,000,000 and more preferably 50,000-5,000,000 since a too low molecular weight results in low viscosity, by which adhesion to the tissue surrounding the applied site may become weak whereas a too high molecular weight makes the production difficult, lowers solubility, makes handling poor due to the too high viscosity in the solution state, makes it difficult to maintain the physical properties during long-term preservation, and the like. Herein, numerical ranges expressed with "-/to" each represent a range that includes the numerical values preceding and following "-/to" as minimum and maximum values, respectively.

Meanwhile, a measurement of a molecular weight of a naturally occurring high molecular weight substance is known to result varied values depending on the measurement method. For example, a weight-average molecular weight measured by gel permeation chromatography (GPC) or gel filtration chromatography (which are also collectively referred to as size exclusion chromatography) is preferably 100,000 or more and more preferably 500,000 or more, while preferably 5,000,000 or less and more preferably 3,000,000 or less, considering the effects shown in the examples of the present invention. The preferable range is 100,000-5,000,000, and more preferably 500,000-3,500,000.

Furthermore, an absolute weight-average molecular weight can be measured, for example, by a GPC-MALS method employing a combination of gel permeation chromatography (GPC) and a multi-angle light scattering detector (Multi Angle Light Scattering: MALS). The weight-average molecular weight (absolute molecular weight) measured by the GPC-MALS method is preferably 10,000 or more, more preferably 30,000 or more and still more preferably 90,000 or more, while preferably 1,000,000 or less, more preferably 800,000 or less, still more preferably 700,000 or less and particularly preferably 500,000 or less, considering the effects shown in the examples of the present invention. The preferable range is 10,000-1,000,000, more preferably 80,000-800,000, still more preferably 90,000-700,000, and particularly preferably 90,000-500,000.

When a molecular weight of a high molecular weight polysaccharide is calculated by the process described above, there is normally a possible measurement error of 10 to 20% or more. For example, a molecular weight of 400,000 may fluctuate within the range of 320,000 to 480,000, a molecular weight of 500,000 may fluctuate within the range of 400,000 to 600,000, and a molecular weight of 1,000,000 may fluctuate within the range of 800,000 to 1,200,000.

A molecular weight of a monovalent metal salt of alginic acid can be measured according to a common method.

Typical conditions for a molecular weight measurement using gel permeation chromatography are as described in the examples herein. For example, GMPW-XL×2+G2500PW-XL (7.8 mm I.D.×300 mm) may be used as the columns, a 200 mM aqueous sodium nitrate solution can be used as the eluent, and pullulan can be used as the molecular weight standard.

Typical conditions for molecular weight measurement using GPC-MALS are as described in the examples herein. For example, a RI detector and a light scattering detector (MALS) can be used as the detectors.

Although a monovalent metal salt of alginic acid has a large molecular weight and a relatively high viscosity when originally extracted from a brown alga, the molecular weight becomes smaller and the viscosity becomes lower during the course of heat drying, purification and the like. Through management of the conditions such as the temperature during the production, selection of the brown alga used as the raw material, processes like molecular weight fractionation during the production and the like, monovalent metal salts of alginic acid having different molecular weights can be produced. Furthermore, it can be mixed with a monovalent metal salt of alginic acid from other lot having different molecular weight or viscosity, so as to give a monovalent metal salt of alginic acid having a molecular weight of interest.

A monovalent metal salt of alginic acid used in the present invention has apparent viscosity of preferably 10 mPa·s-800 mPa·s, more preferably 30 mPa·s-800 mPa·s and still more preferably 50 mPa·s-600 mPa·s. The apparent viscosity is measured by preparing a 1 w/w % solution of a monovalent metal salt of alginic acid dissolved in MilliQ water and using a cone-plate viscometer under the condition of 20° C. The conditions for measuring the apparent viscosity preferably follow the conditions described hereinbelow. Herein, an "apparent viscosity" may simply be referred to as a "viscosity".

Although the alginic acid used in the present invention may be of a natural origin or synthetic, it is preferably derived from a natural origin. Examples of naturally occurring alginic acids include those extracted from brown algae. Although the brown algae containing alginic acid are prominently found along seacoasts worldwide, the algae that can actually be used as raw materials of alginic acid are limited, with typical examples thereof including *Lessonia* found in South America, *Macrocystis* found in North America, *Laminaria* and *Ascophyllum* found in Europe, and *Durvillea* found in Australia. Examples of the brown algae serving as raw materials of alginic acid include genus *Lessonia*, genus *Macrocystis*, genus *Laminaria*, genus *Ascophyllum*, genus *Durvillea*, genus *Eisenia* and genus *Ecklonia*.

3. Endotoxin Reduction Treatment

The monovalent metal salt of alginic acid used in the present invention is preferably a low endotoxin monovalent metal salt of alginic acid. Low endotoxin means that the endotoxin level is low to an extent not to substantially induce inflammation or fever. More preferably, the monovalent metal salt of alginic acid is subjected to an endotoxin reduction treatment.

An endotoxin reduction treatment can be carried out by a known method or a method complying therewith. For example, this treatment can be carried out by the method of Suga et al. involving purification of sodium hyaluronate (see, for example, Japanese Patent Application Laid-open No. H9-324001), the method of Yoshida et al. involving purification of β1,3-glucan (see, for example, Japanese Patent Application Laid-open No. H8-269102), the method of William et al. involving purification of a biopolymer salt such as alginate or gellan gum (see, for example, Published Japanese Translation No. 2002-530440 of PCT International Publication), the method of James et al. involving purification of polysaccharide (see, for example, International Publication No. 93/13136 pamphlet), the method of Lewis et al. (see, for example, U.S. Pat. No. 5,589,591), the method of Hermanfranck et al. involving purification of alginate (see, for example, Appl. Microbiol. Biotechnol. (1994), 40:638-643) or a method complying therewith. The endotoxin reduction treatment of the present invention is not limited thereto, but rather can be carried out by a known method such as washing, purification using filtration with a filter (an endotoxin removing filter, an electrically charged filter, etc.), ultrafiltration or a column (such as an endotoxin adsorption affinity column, a gel filtration column or an ion exchange resin column), adsorption to a hydrophobic substance, a resin, an activated carbon or the like, an organic solvent treatment (such as extraction with an organic solvent or precipitation or deposition by addition of organic solvent), surfactant treatment (see, for example, Japanese Patent Application Laid-open No. 2005-036036) or a suitable combination thereof. A known method such as centrifugation may be suitably combined with these treatment steps. The endotoxin reduction treatment is preferably suitably selected according to the type of alginic acid.

The endotoxin level can be confirmed by a known method, and can be measured using a known method such as a method using a limulus reagent (LAL) or a method using Endospecy (registered trademark) ES-24S set (Seikagaku Corporation).

Although there are no particular limitations on the endotoxin treatment method for the monovalent metal salt of alginic acid contained in the composition of the present invention, as a result of endotoxin reduction treatments, the endotoxin content of the monovalent metal salt of alginic acid when measured using a limulus reagent (LAL) is preferably 500 endotoxin units (EU)/g or less, more preferably 100 EU/g or less, even more preferably 50 EU/g or less and particularly preferably 30 EU/g or less. Sodium alginate that has undergone an endotoxin reduction treatment is a commercially available, for example, as Sea Matrix (registered trademark) (Mochida Pharmaceutical), PRONOVA™ UP LVG (FMC BioPolymer) or the like.

4. Preparation of Solution of Monovalent Metal Salt of Alginic Acid

The composition of the present invention may be prepared by using a solution of monovalent metal salt of alginic acid. The solution of monovalent metal salt of alginic acid can be prepared by a known method or a method complying therewith. In other words, the monovalent metal salt of alginic acid used in the present invention can be produced by a known method such as an acid method or a calcium method using the previously described brown alga. Specifically, for example, following extraction from such a brown alga with an alkaline aqueous solution such as an aqueous sodium carbonate solution, the extract is added with an acid (such as hydrochloric acid or sulfuric acid) to obtain alginic acid, and the alginic acid is subjected to ion exchange to give a salt of alginic acid. An endotoxin reduction treatment is then carried out as previously described. There is no particular limitation on the solvent of the monovalent metal salt of alginic acid provided it is a solvent that can be applied in vivo, and examples of such solvents include purified water, distilled water, ion exchanged water, Milli-Q water, physiological saline and phosphate-buffered saline (PBS). These are preferably sterilized and preferably subjected to an endotoxin reduction treatment. For example, Milli-Q water can be used after sterilizing by filtration.

In a case where the composition of the present invention is provided in a dry state as a lyophilizate or the like, the above-described solvent can be used to prepare it into a solution having fluidity.

Moreover, all of the operations for obtaining the composition of the present invention are preferably carried out in an environment at a low endotoxin level and a low bacterial level. For example, the operations are preferably carried out in a clean bench using sterilized instruments. The instruments used may be treated with a commercially available endotoxin removal agent.

5. Apparent Viscosity of Composition of the Present Invention

Compositions in some aspects of the present invention are in a liquid state having fluidity, namely, a solution state. The composition of a preferable aspect of the present invention has fluidity when applied to an injured fibrocartilaginous tissue part. In a more preferable aspect, the composition of the present invention has fluidity upon making contact with the injured fibrocartilaginous tissue part. In one aspect of the present invention, the composition of the present invention preferably has fluidity that allows injection with a 21 G needle after leaving the composition to stand at 20° C. for an hour. While the apparent viscosity of the composition of the present invention in this aspect is not particularly limited as long as the effect of the present invention can be achieved, it is preferably 10 mPa·s or more, more preferably 100 mPa·s or more, still more preferably 200 mPa·s or more and particularly preferably 400 mPa·s or more since a too low viscosity would weaken adhesion to the tissue surrounding the applied site. It is also preferably 50,000 mPa·s or less, more preferably 20,000 mPa·s or less and still more preferably 10,000 mPa·s or less since a too high apparent viscosity would deteriorate the handing property. An apparent viscosity of 20,000 mPa·s or less would facilitate application with a syringe or the like. Application, however, is also possible even if the apparent viscosity is 20,000 mPa·s or more by using a pressurized or electric filling instrument or other means. The composition of the present invention is preferably in a range of 10 mPa·s-50,000 mPa·s, more preferably 100 mPa·s-30,000 mPa·s, still more preferably 200 mPa·s-20,000 mPa·s, yet still more preferably 400 mPa·s-20,000 mPa·s, and particularly preferably 700 mPa·s-20,000 mPa·s.

In another preferable aspect, it may be 500 mPa·s-10,000 mPa·s, or 2000 mPa·s-10,000 mPa·s. Compositions in some aspects of the present invention have a viscosity that also allows application to a target with a syringe or the like.

The apparent viscosity of a composition containing a monovalent metal salt of alginic acid in a solution state or having fluidity, for example, an aqueous alginate solution, can be measured according to a common method. For example, a coaxial double cylinder type rotational viscometer, a single cylinder type rotational viscometer (Brookfield viscometer), a cone-plate rotational viscometer (a cone-plate viscometer) or the like according to a rotational viscometer method can be used for the measurement. It is preferable to follow the viscosity measurement method of the Japanese Pharmacopoeia (16th edition). According to the present invention, the viscosity measurement is preferably carried out under the condition of 20° C. If the composition of the present invention contains anything that cannot be dissolved in the solvent such as cells as will be described below, the apparent viscosity of the composition is preferably an apparent viscosity free of cells or the like in order to carry out an accurate viscosity measurement.

According to the present invention, an apparent viscosity of a composition containing a monovalent metal salt of alginic acid in a solution state or having fluidity is particularly measured with a cone-plate viscometer. For example, a measurement preferably takes place under the following measurement conditions. A sample solution is prepared with MilliQ water. The measurement temperature is 20° C. The rotation speed of the cone-plate viscometer is 1 rpm for measuring a 1% solution of the monovalent metal salt of alginic acid, 0.5 rpm for measuring a 2% solution, which can be determined so on. The 1% solution of the monovalent metal salt of alginic acid is measured for 2 minutes to obtain the average of the values read during the period from 1 to 2 minutes after the start of said measurement. The 2% solution is measured for 2.5 minutes to obtain an average of the values read during the period from 0.5 to 2.5 minutes after the start of said measurement. An average value of three times of measurements is used as the test value.

The apparent viscosity of the composition of the present invention in a solution state or having fluidity can be adjusted, for example, by controlling the concentration, the molecular weight, the M/G ratio or the like of the monovalent metal salt of alginic acid.

The apparent viscosity of the solution of monovalent metal salt of alginic acid becomes high when the concentration of the monovalent metal salt of alginic acid in the solution is high whereas the viscosity becomes low when the concentration is low. Moreover, the viscosity becomes higher when the molecular weight of the monovalent metal salt of alginic acid is large whereas the viscosity becomes lower when the molecular weight is small.

Since an apparent viscosity of a solution of monovalent metal salt of alginic acid is affected by the M/G ratio, for example, alginate can be suitably selected such that it has an M/G ratio that is more preferable for the viscosity or the like of the solution. The M/G ratio of the alginate used with the present invention is about 0.1-5.0, preferably about 0.1-4.0 and more preferably about 0.2-3.5.

As described above, since the M/G ratio is mainly determined by the species of the alga, the species of the brown alga used as the raw material affects the viscosity of the monovalent metal salt solution of alginic acid. The alginate used with the present invention is preferably derived from a brown alga of genus *Lessonia*, genus *Macrocystis*, genus *Laminaria*, genus *Ascophyllum* and genus *Durvillea*, more preferably derived from a brown alga of genus *Lessonia*, and particularly preferably derived from *Lessonia nigrescens*.

6. Preparation of Composition of the Present Invention

The composition of the present invention is characterized by containing a monovalent metal salt of alginic acid, more preferably by containing a low endotoxin monovalent metal salt of alginic acid. The present inventors found for the first time that when a low endotoxin monovalent metal salt of alginic acid is used to fill an injured meniscus part of a target, the monovalent metal salt of alginic acid per se exerts an effect of regenerating and/or treating the injured meniscus part. The composition contains the low endotoxin monovalent metal salt of alginic acid in an amount to exert the effect of regenerating and/or treating the injured fibrocartilaginous tissue part when being applied to the affected site. The composition of the present invention may, for example, be in a solution state, flaky, powdery or the like.

The composition of the present invention in a solution state or having fluidity may be prepared, for example, by using the above-described solution of monovalent metal salt of alginic acid. Herein, the composition of the present invention in a solution state is also referred to as a "composition having fluidity". In this aspect, the concentration of the monovalent metal salt of alginic acid is at least, preferably 0.1 w/v % or more, more preferably 0.5 w/v % or more and still more preferably 1 w/v % or more of the whole composition, and preferably 0.1 w/v %-5 w/v %, more preferably 0.5 w/v %-5 w/v %, still more preferably 1 w/v %-5 w/v %, yet still more preferably 1 w/v %-3 w/v % and particularly preferably 1.5 w/v %-2.5 w/v %. In another aspect, the concentration of the monovalent metal salt of alginic acid in the composition of the present invention is preferably 0.1 w/w % or more, more preferably 0.5 w/w % or more, still more preferably 1 w/w % or more, and preferably, 0.1 w/w %-5 w/w %, more preferably 0.5 w/w %-5 w/w %, still more preferably 1 w/w %-5 w/w %, yet still more preferably 1 w/w %-3 w/w % and particularly preferably 1.5 w/w %-2.5 w/w %.

While the flaky composition of the present invention is not particularly limited, it may be prepared, for example, by subjecting a composition containing a low endotoxin monovalent metal salt of alginic acid in a sol state or in a gel state to a lyophilization treatment or the like to give a dried product, and shaving or crushing the dried product. The composition containing the monovalent metal salt of alginic acid in a sol state may use, for example, a solution of monovalent metal salt of alginic acid as described above, where the concentration of the solution may, for example, be, but not limited to, 0.5 w/w %-5 w/w %. The composition containing the monovalent metal salt of alginic acid in a gel state may be obtained by adding a later-described crosslinking agent to a solution of monovalent metal salt of alginic acid and homogeneously mixing the resultant to achieve a gel state. The size of the flakes can appropriately be adjusted in accordance with the shape, the property and the like of the injured part. For example, if the flakes are to be adhered to a torn site of a human having a complicated shape, the maximum dimensions of the flaky composition may be 5 mm or less.

Furthermore, the powdery composition of the present invention may be prepared, for example, without particular limitation, by finely crushing the above-described dried product containing the low endotoxin monovalent metal salt of alginic acid. These preparations may be carried out according to a common method.

Compositions in some aspects of the present invention may use cells.

While the cells are not particularly limited as long as the cells are useful for regeneration of a fibrocartilaginous tissue such as a meniscus, examples thereof include meniscus cells, meniscus precursor cells, fibrochondrocytes, fibrocartilage-like cells, chondrocytes, cartilage-like cells, cartilage precursor cells, synovial cells, synovial stem cells, stem cells, stromal cells, mesenchymal stem cells, bone marrow stromal cells, mesenchymal cells, ES cells and iPS cells. More preferably, the cells are at least one selected from bone marrow mesenchymal stem cells, bone marrow stromal cells, meniscus cells, meniscus precursor cells, fibrochondrocytes, fibrocartilage-like cells, chondrocytes, cartilage-like cells, cartilage precursor cells, synovial cells and synovial stem cells. These cells may be any of autologous, homologous, allogeneic or xenogeneic cells. In addition, these cells may be introduced with a gene of a factor for promoting the growth of the cells as described below.

The phrase "to use cells" refers to addition of cells to the composition of the present invention, wherein the cells are prepared, as necessary, by a process in which cells of interest are collected and concentrated from a meniscus, a cartilage, a synovial membrane, a bone marrow, an adipose tissue, an umbilical cord blood or the like, or a process where the cells are cultured to increase the amount thereof. Specifically, the cells are contained in the composition of the present invention, for example, for $1\times10^4$ cells/ml or more, $1\times10^5$ cells/ml or more, preferably $1\times10^4$ cells/ml to $1\times10^8$ cells/ml. The cells may be purchased. In some of other preferable aspects of the present invention, the composition of the present invention does not contain a cell. In some other favorable aspects, the composition of the present invention does not contain bone marrow stromal cells, and may not contain IGF-1 gene-introduced bone marrow stromal cells in another favorable aspect. In another favorable aspect, the composition of the present invention does not contain fibrochondrocytes and/or fibrocartilage-like cells. Even if the composition of the present invention does not contain these cells, regeneration of the injured fibrocartilaginous tissue part is sufficiently good and highly safe without problems of difficulty in availability or handling.

Compositions in some aspects of the present invention may include a substance containing a biological component such as fragments of a fibrocartilaginous tissue such as a meniscus, fibrin clots, platelet-rich plasma (PRP: Platelet Rich Plasma) or the like. Herein, "fragments of a fibrocartilaginous tissue such as a meniscus" can be obtained by making the size of a fibrocartilaginous tissue such as a meniscus smaller by a treatment such as crushing, where the treatment process and the size are not particularly limited. "Fibrin clots" refer to blood clots that can be derived from the peripheral blood of a patient. "Platelet-rich plasma" refers to plasma that contains more platelets than normal blood. Compositions in some aspects of the present invention do not contain a substance containing such a biological component. Compositions in some aspects of the present invention do not contain fragments of a fibrocartilaginous tissue such as a meniscus. Even in these cases, regeneration of the injured fibrocartilaginous tissue part is sufficiently good. They may be prepared and used according to a common method.

The composition of the present invention may also contain a factor for promoting the growth of the cells. Examples of such a factor include BMP, FGF, VEGF (Vascular Endothelial Growth Factor), HGF, TGF-β, IGF-1, PDGF (Platelet-Derived Growth Factor), CDMP (cartilage-derived-morphogenetic protein), KGF (Keratinocyte Growth Factor), CSF, EPO, IL, PRP (Platelet-Rich Plasma), SOX and IF. These factors can be produced by a recombination method or may be purified from a protein composition. Here, compositions of some aspects of the present invention do not contain these growth factors. In some of the other favorable aspects of the present invention, the composition of the present invention does not contain IGF-1. Even if the composition does not contain a growth factor, regeneration of the injured fibrocartilaginous tissue part is sufficiently good and safety is higher than the case where cell growth is actively promoted.

The composition of the present invention may contain factors for suppressing cell death. Examples of a factor that induces cell death include Caspase and TNFα, and examples of a factor for suppressing them include an antibody and siRNA. Such factors for suppressing cell death may be produced by a recombination method or may be purified from a protein composition. Here, compositions in some aspects of the present invention do not contain such factors for suppressing cell death. Even if the composition does not contain the factor for suppressing cell death, regeneration of the injured fibrocartilaginous tissue part is sufficiently good and safety is higher than the case where cell death is actively suppressed.

Furthermore, in one aspect of the present invention, the composition of the present invention does not contain, except the monovalent metal salt of alginic acid, a component that exerts pharmacological action on a fibrocartilaginous tissue. A composition containing a monovalent metal salt of alginic acid but not a component that exerts pharmacological action on a fibrocartilaginous tissue is also able to exert adequate effects for regenerating or treating an injured fibrocartilaginous tissue part, especially an injured meniscus part.

In another aspect of the present invention, the composition of the present invention does not contain a polymer component other than the monovalent metal salt of alginic acid.

In some aspects of the present invention, the composition of the present invention can also contain components ordinarily used in pharmaceuticals and medical instruments, such as other pharmaceutically active ingredients and commonly used stabilizers, emulsifiers, osmotic pressure adjusters, buffers, isotonic agents, preservatives, pain relievers or colorants as necessary.

7. Curing of Composition of the Present Invention

In one aspect of the present invention, the composition of the present invention in a solution state or having fluidity is used such that it is used so as to be at least partially cured after being applied to an injured fibrocartilaginous tissue part.

"At least partially cured" means to bring a crosslinking agent into contact with at least a part of the composition of the present invention having fluidity so as to gel and solidify at least a part of the composition making contact with the crosslinking agent. Preferably, the crosslinking agent is brought into contact with at least a part of the surface of the composition of the present invention having fluidity so as to cure at least a part of the composition of the present invention. In one aspect of the present invention, "at least partially cured" may mean that not the whole composition is gelled and that at least 10% or at least 30% of the whole composition is not gelled. For example, in "an aspect where at least 10% of the composition is not gelled", the proportion of the ungelled composition may be such that at least 10% of the volume of the composition in a given container is not gelled when the container is filled with a low endotoxin sodium alginate and a crosslinking agent and left to stand for a predetermined period of time in vitro according to the same usage method and the same ratio of the crosslinking agent as those employed for filling an injured meniscus part, where the ungelled part may be represented by suction of at least 50% of the volume of the composition in the container using a syringe with a 21 G needle. "At least a part of the surface of the composition" refers to, for example, an opening in the surface of an injured fibrocartilaginous tissue part, preferably, a part of the surface of the composition of the present invention applied to an injured fibrocartilaginous tissue part. Solidification of at least a part of the surface of the composition by gelation can effectively prevent leakage of the composition from the injured fibrocartilaginous tissue part.

Preferably, the composition of the present invention in a solution state or having fluidity does not contain the crosslinking agent in an amount that results curing of the composition before application to the injured fibrocartilaginous tissue part of a target. More preferably, the composition of the present invention having fluidity does not contain the crosslinking agent in an amount that results curing of the composition upon making contact with the injured fibrocartilaginous tissue part of a target. Therefore, the composition of the present invention in a solution state or having fluidity may contain the crosslinking agent in an amount that does not result curing of the composition even after a predetermined period of time. Herein, a predetermined period of time refers to, but not particularly limited to, preferably about 30 minutes to 24 hours. The phrase "does not contain a crosslinking agent in an amount that results curing of the composition" may be represented, for example, by the composition being injectable with a syringe with a 21 G needle after being left to stand at 20° C. for 12 hours. Compositions in some aspects of the present invention are free of the crosslinking agent.

In one preferable aspect of the present invention, when a composition of the present invention in a solution state or having fluidity is used, the composition of the present invention is brought into contact with a crosslinking agent after the composition has been applied to an injured fibrocartilaginous tissue part of a target. Herein, the phrase "brought into contact with a crosslinking agent after the composition has been applied to an injured fibrocartilaginous tissue part of a target" means that the contact of the composition of the present invention with the crosslinking agent and the application of the composition to the injured meniscus part of the target are carried out at separate timings, and that the contact of the composition of the present invention with the crosslinking agent is carried out after the application of the composition to the injured fibrocartilaginous tissue part of the target. In more preferable aspect, the contact of the composition of the present invention with the crosslinking agent for curing the composition of the present invention having fluidity is carried out after the contact of the composition with the injured fibrocartilaginous tissue part of the target. Accordingly, in these aspects, the application of the composition of the present invention to the injured fibrocartilaginous tissue part of the target does not include a case where the composition of the present invention is mixed with the crosslinking agent before the application, or a case where the composition of the present invention and the crosslinking agent are placed in separate tubes, cannulas, syringes or the like and simultaneously applied to the injured fibrocartilaginous tissue part of the target.

In one preferable aspect of the present invention that uses the composition of the present invention having fluidity, the composition is cured by bringing the crosslinking agent into contact with at least a part of the surface of the composition. More preferably, the composition of the present invention having fluidity is applied to the injured fibrocartilaginous tissue part of the target, and then the composition is cured by bringing the crosslinking agent into contact with at least a part of the surface of the composition. As described above, the composition of the present invention having fluidity preferably does not contain a crosslinking agent in an amount that allows curing of the composition before it is applied to an injured fibrocartilaginous tissue part of a target, more specifically, before it makes contact with the injured fibrocartilaginous tissue part.

The crosslinking agent used in the present invention is not particularly limited as long as it can crosslink a solution of monovalent metal salt of alginic acid. Examples of the crosslinking agent include divalent or higher valent metal ion compounds such as $Ca^{2+}$, $Mg^{2+}$, $Ba^{2+}$ and $Sr^{2+}$ and crosslinking reagents having 2 to 4 amino groups in a molecule thereof. Specific examples of the divalent or higher valent metal ion compounds include $CaCl_2$, $MgCl_2$, $CaSO_4$ and $BaCl_2$. Specific examples of the crosslinking reagents having 2 to 4 amino groups in a molecule thereof include diaminoalkanes optionally having a lysyl group (—COCH (NH$_2$)—(CH$_2$)$_4$—NH$_2$) on a nitrogen atom, namely, diaminoalkane and derivatives in which the amino group is substituted with a lysyl group to form a lysylamino group, coretely, include diaminoethane, diaminopropane and N-(lysyl)-diaminoethane. A divalent or higher valent metal ion compound is preferable and a $CaCl_2$ solution is more preferable for reasons such as availability and strength of the gel.

In one of some aspects of the present invention, the timing of bringing the crosslinking agent into contact with the surface of the composition of the present invention in a solution state or having fluidity is preferably after the application of the composition of the present invention to the injured fibrocartilaginous tissue part. A method for bringing the crosslinking agent (for example, a divalent or higher valent metal ion) into contact with at least a part of the composition of the present invention is not particularly limited and may be, for example, a method in which a solution of the divalent or higher valent metal ion is applied to the surface of the composition with a tube, a cannula, a syringe, a spray or the like. For example, a crosslinking agent may be continuously and slowly be applied to the surface of the composition applied to the injured fibrocartilaginous tissue part by spending several seconds to 10-odd seconds. Thereafter, if necessary, a treatment for removing the crosslinking agent remaining in the vicinity of the site where the crosslinking agent has been added may be carried out. The crosslinking agent may be removed, for example, by washing the applied site with physiological saline or the like.

Preferably, the amount of the crosslinking agent used for the composition of the present invention in a solution state or having fluidity is appropriately adjusted considering the amount of the composition of the present invention applied, the area of the surface of the composition applied to the injured fibrocartilaginous tissue part, the size of the applied site of the injured fibrocartilaginous tissue part, and the like. In order not to strongly affect the tissue surrounding the composition-applied site with the crosslinking agent, the amount of the crosslinking agent used is controlled not to be too much. The amount of the divalent or higher valent metal ion used is not particularly limited as long as the surface of the composition containing the monovalent metal salt of alginic acid can be solidified. If, for example, a 100 mM $CaCl_2$) solution is used and the area of the surface of the composition applied to the fibrocartilaginous tissue is a diameter of about 1 mm, the amount of the $CaCl_2$) solution used is preferably about 0.3 ml-5.0 ml, and more preferably about 0.5 ml-3.0 ml. If the area of the surface of the composition applied to the fibrocartilaginous tissue is a diameter of about 1 cm, the amount of the 100 mM $CaCl_2$) solution used is preferably about 0.3 ml-10 ml and more preferably about 0.5 ml-6.0 ml. The amount can suitably be increased or decreased while observing the state of the composition of the present invention at the applied site.

In the case calcium is contained in the crosslinking agent, a higher calcium concentration is known to result in rapid gelation and a harder gel formation. However, since calcium is cytotoxic, if the concentration is too high, it may have a risk of adversely affecting the action of the composition of the present invention to regenerate the injured fibrocartilaginous tissue part. Therefore, if, for example, a $CaCl_2$) solution is used to solidify the surface of a composition containing a monovalent metal salt of alginic acid, the concentration is preferably set to 25 mM-200 mM and more preferably 50 mM-150 mM.

In one preferable aspect of the present invention in which the composition of the present invention in a solution state or having fluidity is used, the crosslinking agent remaining at the added site after adding the crosslinking agent to the composition and leaving the resultant to stand for a predetermined period of time, is preferably removed by washing with physiological saline or the like. While the predetermined period of time for leaving the composition to stand is not particularly limited, it is preferably left to stand for about 30 seconds or longer, about a minute or longer, more preferably about 4 minutes or longer so as to gel the surface of the composition. Alternatively, it is preferably left to stand for about 1-10 minutes, more preferably about 4-10 minutes, about 4-7 minutes and still more preferably about 5 minutes. The composition of the present invention and the crosslinking agent are preferably in contact during this predetermined period of time, where the crosslinking agent may additionally be added so as to prevent the liquid surface of the composition from drying.

8. Application of Composition of the Present Invention

The composition of the present invention can be applied to an injured fibrocartilaginous tissue part of a human or an organism other than a human, for example, a bird or a non-human mammal (for example, bovine, monkey, cat, mouse, rat, guinea pig, hamster, pig, dog, rabbit, sheep, goat or horse).

Compositions of the present invention in some aspects are preferably in a form of liquid having fluidity, namely, a solution, upon application to a fibrocartilaginous tissue. According to the present invention, the phrase "having fluidity" means to have a property of freely changing into any shape, which may be a viscous sol state. For example, it preferably has fluidity that allows the composition to be filled in a syringe and injected into an injured fibrocartilaginous tissue part. At the same time, the composition preferably has a viscosity such that it is unlikely to flow out from the applied tissue. According to the present invention, the phrases "in a solution state" and "having fluidity" also include a sol state. Furthermore, in one of some aspects of the present invention, the composition preferably has fluidity so that it can be injected into an injured fibrocartilaginous tissue part with a syringe equipped with a 14 G-26 G needle, a cannula or an arthroscopically assisted injection instrument, and more preferably the composition can be injected with a 21 G needle, after being left to stand at 20° C. for an hour. If the composition of the present invention is provided in a dry state as a lyophilizate or the like, it can be made into a composition having the above-described fluidity by using a solvent or the like upon application.

The composition of the present invention in a solution state or having fluidity can easily be applied to an injured fibrocartilaginous tissue part with a tube, a cannula, a syringe, a pipette for gel, a specialized syringe, a specialized injector, a filling instrument or the like. Since application with a syringe is difficult when the viscosity of the composition of the present invention is high, a pressurized or electric syringe or the like may be used. Even without a syringe or the like, application to an injured fibrocartilaginous tissue part can be carried out, for example, with a spatula, a stick or the like. When a syringe is used for injection, for example, a 14 G-27 G or 14 G-26 G needle is preferably used.

While the amount of the composition of the present invention in a solution state or having fluidity to be applied can be determined according to the capacity of the site of the fibrocartilaginous tissue of the target to be applied. The amount to be applied may be, for example, but not limited to, 0.01 ml-10 ml, more preferably 0.1 ml-5 ml and still more preferably 0.2 ml-5 ml. When the composition of the present invention is to be applied to an injured meniscus part, it is preferably injected so as to sufficiently fill the capacity of the injured part of the injured meniscus part.

After the composition of the present invention in a solution state or having fluidity is applied to the injured fibrocartilaginous tissue part, at least a part of the composition can be cured with a crosslinking agent as described above. For example, a divalent or higher valent metal ion compound such as a $CaCl_2$ solution can be used to cure the surface of the composition.

In one aspect of the present invention, the composition of the present invention in a solution state or having fluidity is also applicable to injured fibrocartilaginous tissue parts with various shapes, and can also favorably be used for a sutured torn or injured part. Application of the composition of the present invention to a sutured torn site can promote regeneration of the injury as compared to the case where the composition of the present invention is not used. In the examples of the present invention, the composition of the present invention was suggested to be effective even for an injury in the avascular area where the regeneration capacity is low and where regeneration has conventionally been considered impossible even by suturing. Therefore, in a preferable aspect of the present invention, the composition of the present invention can favorably be used for treating an injury in an avascular area, if necessary, in combination with suture.

In another aspect of the present invention, the composition of the present invention is powdery or flaky. In this aspect, the composition of the present invention may be applied to an injured fibrocartilaginous tissue part using, but not particularly limited to, a spray or the like. Since the powdery or flaky composition can easily be applied with a tube, a cannula, a spray or the like, it can favorably be used, for example, for a relatively small injured part or an injured part at a location or an angle difficult to bring a solution into contact. Moreover, the powdery or flaky composition can be brought into contact with an injured part with a tube, a cannula, a spray or the like with good adhesiveness to the injured part, and moisture can be added to the composition after the adhesion for gelation.

While the method for applying the composition of the present invention to the injured fibrocartilaginous tissue part is not particularly limited, the composition of the present invention is preferably applied to the injured fibrocartilaginous tissue part by using a tube, a cannula, a syringe, a filling instrument, a spray or the like after exposing the affected site by a known surgical process under direct vision, or under an arthroscope or an endoscope. In one preferable aspect, the needle of the syringe, the tube, the cannula, the filling instrument or the like can be inserted, for example, from the front, the back or the side of the knee toward the injured meniscus part to apply the composition of the present invention.

The number of times and the frequency of the application of the composition of the present invention can be increased or decreased according to the symptoms and the effect. For example, it may be a single application, or regular application once in a month to a year.

Even when the composition of the present invention is provided without the above-described cells or growth factors, the composition of the present invention may be used in combination with the above-described cells, the substance containing a biological component, growth factors, cell death suppressing factors, and other drugs mentioned below upon application to the injured fibrocartilaginous tissue part.

The composition of a preferable aspect of the present invention exerts the effects of suppressing degenerative changes in the meniscus and promoting regeneration by being applied to the injured meniscus part. Therefore, in one aspect of the present invention, the composition of the present invention can favorably be used as a composition for treating a meniscus injury.

One of the preferable aspects of the composition of the present invention is a composition for suppressing degeneration of a meniscus. "Degeneration of a meniscus" means the same as described for a "degenerative meniscus" above. In the present description, "suppression of degeneration" does not necessarily mean a situation with no degeneration as long as the degenerative change is suppressed as compared to an untreated case.

One aspect of the composition of the present invention is a composition for regenerating a fibrocartilaginous tissue, more preferably a composition for regenerating a meniscus.

The term "regeneration of a meniscus" also comprises suppression of the degeneration of the meniscus. In one of the preferable aspects of the present invention, the component of a fibrocartilage regenerated by applying the composition of the present invention is close to that of an original normal fibrocartilage.

Moreover, the composition of the preferable aspect of the present invention can be used for treating, preventing or suppressing recurrence of a fibrocartilaginous tissue injury. Herein, "treatment, prevention or suppression of recurrence" comprise treatment, prevention, suppression of recurrence, reduction, suppression, improvement, removal, reduction in onset rate, delay of onset, suppression of progress, amelioration of severity, reduction in recurrence rate, delay of recurrence, alleviation of clinical symptoms and the like. According to the present invention, "prevention" not only refers to prevention of the onset of the condition or the disease but also include delay of the onset and reduction in the onset rate. Furthermore, "suppression of recurrence" not only refers to complete suppression of the condition or the disease, but also include delay of the recurrence and reduction in the recurrence rate. Unless otherwise specified, a "treatment" as used herein means to include "treatment, prevention or suppression of recurrence" as described above.

The preferable aspects of these compositions of the present invention, the methods of using the composition, and the like are as described above.

In one aspect of the present invention, the composition of the present invention is used in a method for treating a fibrocartilaginous tissue injury described below.

9. Method of Treatment

The present invention provides a method for treating, preventing or suppressing recurrence of an injured fibrocartilaginous tissue part, especially an injured meniscus part by using the above-described composition of the present invention. More preferably, a method of treatment of the present invention is a method for treating, preventing or suppressing recurrence of degeneration of a fibrocartilaginous tissue and/or an injury of a fibrocartilaginous tissue, the method comprising applying a composition containing a monovalent metal salt of alginic acid, more preferably a composition containing a low endotoxin monovalent metal salt of alginic acid to an injured fibrocartilaginous tissue part of a target in need of said treatment, prevention or suppression of recurrence.

While meniscus resection and meniscus suturing are the commonly employed methods for meniscus injuries, they have difficulty in completely recovering the injured part and thus the treatments have not been sufficiently satisfactory. Accordingly, a variety of methods of treatment have been studied so far. For example, a cell therapy in which synovial cells collected from autologous synovial membrane are cultured and then transplanted to an injured part is undergoing development. Since, however, autologous cells are collected and transplanted into the injured part in this method, this method requires two stages of procedures, namely, a procedure for taking the cells out from the body of the patient and a procedure for implanting the cells into the injured part, which will impose burdens on the patient and the medical practitioner. Therefore, there has been a demand for a novel method for treating a meniscus injury, which is highly effective with a simple procedure and less burden on the patient and the medical practitioner. The method of treatment of the present invention was made based on such an issue.

A method of treatment in one aspect of the present invention comprises the following steps.

(a) enabling visual recognition of the injured fibrocartilaginous tissue part through an incision or with an arthroscope or an endoscope;
(b) if necessary, removing an unnecessary tissue from the injured fibrocartilaginous tissue part and the peripheral part thereof;
(c) if necessary, suturing the injured fibrocartilaginous tissue part;
(d) applying the composition of the present invention to the injured fibrocartilaginous tissue part;
(e) if necessary, adding a crosslinking agent to the surface of the applied composition, and leaving the resultant for a predetermined period of time to bring the composition into contact with the crosslinking agent;
(f) if necessary, washing the site where the crosslinking agent had been added; and
(g) if necessary, closing the incision or the opening resulting from insertion of the arthroscope, the endoscope or other instrument.

According to the method of treatment of the present invention, the injured fibrocartilaginous tissue part is made endoscopically visible or directly visible through an incision or by using means such as an arthroscope or an endoscope, before the application of the composition of the present invention to the injured fibrocartilaginous tissue part. An arthroscope is one kind of endoscope for observing the condition of the joint.

The method of treatment of the present invention may comprise the step of removing at least a part of the fibrocartilaginous tissue prior to the application of the composition of the present invention to the injured fibrocartilaginous tissue part. Herein, "unnecessary tissue of the injured fibrocartilaginous tissue part and the peripheral part thereof" refers to the lesion tissue, the injured part, the torn site or the degenerative part of the injured fibrocartilaginous tissue part, or the abnormal tissue part of the peripheral part thereof. According to the method of treatment of the present invention, such an unnecessary tissue is preferably removed by resection or the like to freshen the peripheral part. Herein, "if necessary" means to arbitrarily determine the propriety of this step and the area to be removed depending on the condition of the target (subject). For example, if the peripheral part of the meniscus defective part prior to operation is a normal meniscal tissue, this step of removing the injured meniscus part is unnecessary. This step can promote earlier regeneration of the normal fibrocartilaginous tissue.

The method of treatment of the present invention may comprise the step of suturing the injured fibrocartilaginous tissue part prior to the application of the composition of the present invention. For example, if the injured meniscus part is largely defected, the injured part can be sutured to be fixed before the composition of the present invention is applied thereto so that further expansion of the meniscus injury caused by a load or exercise can be suppressed to realize an effective treatment. According to the present invention, an injured fibrocartilaginous tissue part can be sutured by a common method, whose examples include, but not particularly limited to, an inside-out repair technique, an outside-in repair technique, an all-inside repair technique and a hybrid technique employing multiple techniques (Knee Surg Relat Res 2014; 26(2):68-76).

The composition of the present invention is preferably applied to an injured fibrocartilaginous tissue part by injection so as to adequately fill the capacity of the cavity at the affected site. Moreover, for example, if the composition of the present invention in a solution state or having fluidity is applied to a meniscus injury, it is preferable to implant the composition such that the liquid surface of the composition becomes approximately the same level as the surrounding meniscal tissue at the meniscus defective part. Herein, the term "to apply" is used to comprise the term "to implant".

When the composition of the present invention is in a solution state or has fluidity, at least a part of the composition is preferably cured by adding a crosslinking agent to the surface of the composition applied. While the predetermined period of time for leaving the crosslinking agent added to the composition is not particularly limited, in some aspects of the present invention, it is left to stand for preferably about 1 minute or longer and more preferably for about 5 minutes or longer to gel the surface of the composition. Alternatively, it is preferable to leave the crosslinking agent added to the composition for about 1 minute to about 10 minutes, more preferably about 3 minutes to about 10 minutes, about 4 minutes to about 7 minutes, and still more preferably about 5 minutes. The composition and the crosslinking agent are preferably in contact with each other during this predetermined period of time, where the crosslinking agent may additionally be added so as to prevent the liquid surface of the composition from drying.

If necessary, the method of treatment of the present invention preferably comprises the step of washing the site where the crosslinking agent had been added, for example, with physiological saline or the like after adding the crosslinking agent to the composition and leaving the resultant to stand for a predetermined period of time. The method preferably comprises this step if the crosslinking agent is anticipated to affect the organism.

If necessary, the method of treatment of the present invention may comprise the step of closing the incision or the opening resulting from insertion of the arthroscope, the endoscope or other instrument, by suturing or by a procedure pursuant thereto. Herein, "other instrument" is not particularly limited as long as it is an instrument generally used for surgery, and examples thereof include instruments used for endoscopic surgery such as an instrument for resecting tissue, a suturing instrument and forceps.

If necessary, the affected site may be washed prior to the application of the composition of the present invention. "To wash an affected site" means to remove the blood component, other unnecessary tissue and the like, for example, with physiological saline at the site to be applied with the composition of the present invention. After the washing, the affected site is preferably dried, for example, by wiping off the remaining unnecessary liquid component, and then applied with the composition of the present invention.

Application of the composition of the present invention to the injured meniscus part is expected to regenerate the meniscus to restore the component and the strength close to those of the original meniscal tissue. For example, while a normal meniscus is considered to contain cells like fibrocartilage-like cells (fibrocartilage cells) and cartilage-like cells (chondrocyte-like cells), the injured meniscus part is expected to have a component and a number of cells close to those in the normal meniscus.

When a meniscus is sutured, platelet-rich plasma (PRP) or fibrin clot may be used in combination in order to enhance the regeneration effect. The composition of the present invention may be used together with PRP or fibrin clot, or in place of them to be used in combination with suturing of the meniscus. In the examples of the present invention, the composition of the present invention was suggested to be effective for an injured part in an avascular area of a meniscus. Accordingly, the composition of the present invention is expected to exert a regeneration effect when applied, if necessary, in combination with suturing, even for an injury in an avascular area where suturing has conventionally been considered ineffective.

According to the present invention, "to apply to an injured fibrocartilaginous tissue part" means to use the composition or the like to make contact with the injured fibrocartilaginous tissue part, where the composition of the present invention is preferably injected into the injured fibrocartilaginous tissue part so as to embed the sutured site or the defective part.

According to the present invention, a fibrocartilaginous tissue injury is, for example, at least one condition or disease selected from the group consisting of a meniscus injury, a traumatic meniscus injury, a degenerative meniscus, a discoid meniscus, osteochondritis dissecans, cartilage degeneration, an intracapsular ligament injury, a sports injury, osteoarthritis and a triangular fibrocartilage complex injury and/or degeneration. In some aspects of the present invention, a fibrocartilaginous tissue injury targeted to be treated by the method of treatment of the present invention is at least one condition or disease selected from the group consisting of a meniscus injury, a traumatic meniscus injury, a degenerative meniscus, a discoid meniscus and a triangular fibrocartilage complex injury and/or degeneration, and more preferably is at least one condition or disease selected from the group consisting of, a meniscus injury, a traumatic meniscus injury, a degenerative meniscus and a discoid meniscus.

Furthermore, one of some aspects of the present invention provides a method for suppressing degenerative changes in a meniscus by using the composition of the present invention. In addition, one preferable aspect of the present invention provides a method for regenerating an injured fibrocartilaginous tissue part by using the composition of the present invention.

Preferable aspects of the composition of the present invention, a specific method for applying the composition to an injured fibrocartilaginous tissue part, a method for curing the composition, meanings of the terms and the like are as described above. The method of treatment of the present invention may be carried out by appropriately combining with other method or agent for treating a fibrocartilaginous tissue.

Furthermore, a co-administered drug, for example, an antibiotic such as streptomycin, penicillin, tobramycin, amikacin, gentamycin, neomycin or amphotericin B, an anti-inflammatory drug such as aspirin, a non-steroidal anti-inflammatory drug (NSAID) or acetaminophen, a proteinase, a corticosteroid drug or a HMG-CoA reductase inhibitor such as simvastatin or lovastatin can be filled before, simultaneously with or after application of the composition of the present invention to the injured fibrocartilaginous tissue part. These drugs may also be mixed into the composition of the present invention and be used. Alternatively, they may be administered orally or parenterally for co-administration. In addition, if necessary, a muscle relaxant, an opioid analgesic, a neurogenic pain alleviating drug or the like may be administered orally or parenterally for co-administration. In another aspect of the present invention, the composition of the present invention may be administered without a HMG-CoA reductase inhibitor.

Moreover, in some aspects of the present invention, the above-described cells can be applied to the injured fibrocartilaginous tissue part together with the composition of the present invention. Alternatively, in some aspects of the present invention, the above-described substance containing a biological component, a factor for promoting the growth of cells or a cell death suppressing factor can be applied to the injured meniscus part together with the composition of the present invention. In another aspect of the present invention, the composition of the present invention is preferably not used in combination with the above-described cells. Alternatively, in another aspect of the present invention, the composition of the present invention is preferably not used in combination with the above-described substance containing a biological component, a factor for promoting the growth of cells or a cell death suppressing factor. In another aspect, the composition of the present invention is preferably not used in combination with fragments of a fibrocartilaginous tissue such as a meniscus. In other aspects, the composition of the present invention is preferably not used in combination with bone marrow stromal cells, preferably not used in combination with bone marrow stromal cells introduced with IGF-1 gene, or preferably not used in combination with IGF-1. In yet another aspect, the composition of the present invention is preferably not used in combination with fibrochondrocytes and/or fibrocartilage-like cells. The composition of the present invention can promote regeneration of an injured fibrocartilaginous tissue part such as a meniscus without these cells, substance or factor.

The present invention also relates to use of a monovalent metal salt of alginic acid for producing a composition of the present invention, more preferably, to use of a low endotoxin monovalent metal salt of alginic acid for producing a composition of the present invention.

The use of the present invention is use of a monovalent metal salt of alginic acid for producing a composition for treating, preventing or suppressing recurrence of a fibrocartilaginous tissue injury, wherein the composition is used so as to be applied to an injured fibrocartilaginous tissue part of a target.

The present invention provides a monovalent metal salt of alginic acid for use in treating, preventing or suppressing recurrence of a fibrocartilaginous tissue injury by applying a composition comprising the monovalent metal salt of alginic acid to the injured fibrocartilaginous tissue part of a target, and further provides a low endotoxin monovalent metal salt of alginic acid for use in treating, preventing or suppressing recurrence of a fibrocartilaginous tissue injury by applying a compositing comprising the low endotoxin monovalent metal salt of alginic acid to the injured fibrocartilaginous tissue part of a target in need of treating, preventing or suppressing recurrence of the fibrocartilaginous tissue injury.

According to a method of the present invention for treating a meniscus injury in one aspect of the present invention, the degree of the meniscus injury of the target may be diagnosed before performing the method of treatment of the present invention so as to select an appropriate method of treatment according to the diagnosis results. While the method of such diagnosis is not particularly limited, maneuver tests are widely used. Many maneuver tests exist for testing a meniscus injury and they are often combined so as to improve the diagnostic value. For example, the presence or the absence of induction of pain and click is regarded as pathologic findings in the McMurray test.

Besides maneuver tests, nuclear magnetic resonance imaging (MRI) or the like can also be employed for examination. When an injured part is observed by MRI, a meniscus which usually has completely low signal (low intensity)

in a T1-weighted image is changed to have high signal (high intensity) at the degenerated or injured part. This diagnosis, however, may be difficult due to the presence of the popliteus tendon posterior and lateral to the lateral meniscus.

The levels of the abnormal signal intensity in the meniscus as determined by MRI may be classified according to the Mink classification into the following grades, where Grade 3 is regarded as a meniscus injury.

Grade 1: Dotted/spotted areas of signal intensity that do not extend to the articular surface Grade 2: Linear area of signal intensity that does not extend to the articular surface Grade 3: Area of signal intensity that extends to the articular surface In one aspect of the present invention, the method of the present invention for treating a meniscus injury preferably targets a patient of Grade 3 according to the Mink classification as a target to be treated.

10. Formulation, Kit

The present invention provides a kit for treating an injured fibrocartilaginous tissue part.

The kit of the present invention can comprise a composition of the present invention. The composition of the present invention contained in the kit of the present invention is in a solution state or a dry state, preferably in a dry state, more preferably a lyophilizate, and particularly preferably lyophilized powder. If the composition of the present invention is a lyophilizate, the kit preferably contains a dissolving solvent (for example, injectable water).

The kit of the present invention may further comprise a crosslinking agent.

The kit of the present invention may further comprise a crosslinking agent, a syringe, a needle, a pipette for gel, a specialized filling unit, an instruction manual and the like.

A specific examples of a preferable kit is a kit of a single pack comprising (1) a vial in which a lyophilizate of a low endotoxin sodium alginate is filled, (2) an ampule in which a solvent such as injectable water as a dissolving liquid is filled, (3) an ampule in which a divalent or higher valent metal ion compound such as a calcium chloride solution as a crosslinking agent is filled, and else. Another example is a kit in which a monovalent metal salt of alginic acid is filled in one compartment of a syringe composed of two integrally formed compartments divided by a partition, while a solvent as a dissolving liquid or a solution containing a crosslinking agent is filled in the other compartment, so that the partition between the compartments can be penetrated easily upon use to enable the contents of both compartments to be mixed and dissolved upon use. Another example is a kit in which a solution of monovalent metal salt of alginic acid is filled in a pre-filled syringe so that it can be administered directly upon use without requiring a preparation procedure. Another example is a kit in which an alginate solution and a crosslinking agent are filled in separate syringes and packaged together in a single pack. Alternatively, it may be a kit comprising a vial filled with a solution of monovalent metal salt of alginic acid, an ampule in which a crosslinking agent is filled, and else. Alternatively, it may be a set comprising a container in which a flaky or powdery composition of the present invention is filled and a filling instrument such as a spray. The "composition of the present invention", the "crosslinking agent", the "syringe" and the like are as described above.

The kit of the present invention can, for example, be used in a method of treatment of the present invention.

EXAMPLES

While the present invention will be described in more detail by the following examples, the present invention should not be understood to be limited to the following examples.

Example 1: Effect of Administration of Low Endotoxin Sodium Alginate into Rabbit Meniscus Defect A rabbit meniscus defect was filled with a low endotoxin sodium alginate solution to evaluate the effect.

1-(1) Preparation of Low Endotoxin Sodium Alginate Solution

Sodium alginate (Mochida Pharmaceutical) was used to prepare a low endotoxin sodium alginate solution. The endotoxin content was less than 50 g/EU. The apparent viscosity and the weight-average molecular weight of the low endotoxin sodium alginate was as shown in Table 1. The apparent viscosity of the sodium alginate was measured by employing a rotational viscometer method (cone-plate rotational viscometer) according to the viscosity measurement method of the Japanese Pharmacopoeia (16th edition). Specific measurement conditions were as follows. Sample solutions were prepared using MilliQ water. As the measurement instrument, a cone-plate rotational viscometer (viscosity/viscoelasticity measurement device RheoStress RS600 (Thermo Haake GmbH) sensor: 35/1) was used. The rotation speed was 0.5 rpm. The measurement was carried out for 2.5 minutes to obtain an average of the values read during the period from 0.5 to 2.5 minutes after the start of said measurement. An average value of three times of measurements was used as the measured value. The temperature for the measurements was 20° C.

The weight-average molecular weight of the sodium alginates was measured by two types of measurement methods, namely, gel permeation chromatography (GPC) and GPC-MALS. The measurement conditions were as follows.

[Pretreatment Process]

After the sample was dissolved in an eluent, the resultant was filtrated through a 0.45 μm membrane filter to obtain a measurement solution (A) Gel Permeation Chromatography (GPC) Measurement

[Measurement Conditions (Relative Molecular Weight Distribution Measurement)]

Columns: TSK gel GMPW-XL×2+G2500PW-XL (7.8 mm I.D.×300 mm×3 columns)

Eluent: 200 mM aqueous sodium nitrate solution

Flow rate: 1.0 mL/min

Concentration: 0.05%

Detector: RI detector

Column temperature: 40° C.

Injected amount: 200 μL

Molecular weight standard: Pullulan standard, glucose (B) GPC-MALS Measurement

[Refractive Index Increment (Dn/Dc) Measurement (Measurement Conditions)]

Differential refractometer: Optilab T-rEX

Measurement wavelength: 658 nm

Measurement temperature: 40° C.

Solvent: 200 mM aqueous sodium nitrate solution

Sample concentrations: 0.5-2.5 mg/mL (5 concentrations)

[Measurement Conditions (Absolute Molecular Weight Distribution Measurement)]

Columns: TSKgel GMPW-XL×2+G2500PW-XL (7.8 mm I.D.×300 mm×3 columns)
Eluent: 200 mM aqueous sodium nitrate solution
Flow rate: 1.0 mL/min
Concentration: 0.05%
Detector: RI detector, light scattering detector (MALS)
Column temperature: 40° C.
Injected amount: 200 μL

TABLE 1

| Apparent viscosity (mPa · s) | | Weight-average molecular weight | | M/G ratio |
|---|---|---|---|---|
| 1 w/w % | 2 w/w % | GPC | GPC-MALS | |
| 300-600 | 3000-6000 | 1,100,000-1,800,000 | 200,000-400,000 | 0.2-1.8 |

The low endotoxin sodium alginate was dissolved in physiological saline to prepare a 2 w/w % solution.

1-(2) Preparation of Rabbit Meniscus Defect (Punched Out) Model

A columnar defect with a diameter of 2 mm was made through each of the anterior horns of the medial menisci in both knees of 30 Japanese white rabbits weighing 3.5±0.2 kg with a biopsy punch, to obtain meniscus defect models.

The meniscus defect in the left knee of each rabbit was left untreated as an untreated control (Group I: control group).

1-(3) Filling Low Endotoxin Sodium Alginate Solution

The 2 w/w % low endotoxin sodium alginate solution prepared in 1-(1) above was used to fill the meniscus defect in the rabbit right knee. A 100 mM calcium chloride solution was added to the top and the bottom of the low endotoxin sodium alginate solution filling the defect for about 10 seconds to gel the surface. Thereafter, the site applied with the calcium chloride solution was washed with physiological saline (Group II: treatment group). Owing to the contact with the calcium chloride solution, the sodium alginate solution did not come off from the defective part.

The rabbits were euthanatized ten each at 3, 6 and 12 weeks after the operation to collect the menisci for gross observation, histological evaluation and measurement of mechanical strength.

1-(4) Gross Observation

The collected menisci were gross observed. In addition, they were scored according to "Criteria to Quantitatively Evaluate the Volume and Quality of Regenerated Tissues in Gross Observation" shown in Table 1 of "The American Journal of Sports Medicine, (2010) Vol. 38 No. 4, p. 740-748". Specifically, each of the five criteria, namely, "width of the regenerated tissue in the axial plane", "sharpness of the free edge of the regenerated tissue", "color of the regenerated tissue", "smoothness of the regenerated tissue surface" and "stiffness of the regenerated tissue" was evaluated in three scores of 0, 1 and 2, for comparison based on the total score. Score 2 is the best score. Specific evaluation criteria used for scoring are shown in the table below.

TABLE 2

| | Score 0 | Score 1 | Score 2 |
|---|---|---|---|
| Width of the regenerated tissue in the axial plane | Fair (less than one-third the normal width) | Good (one-third to two-thirds the normal width) | Excellent (more than two-thirds the normal width) |
| Sharpness of the free edge of the regenerated tissue | Round | Dully wedged | Sharply wedged like the normal meniscus |
| Color of the regenerated tissue | Reddish | Yellowish | White |
| Smoothness of the regenerated tissue surface | Rough and dull | Partially smooth and glossy | Smooth and glossy |
| Stiffness of the regenerated tissue | Soft | Partially stiff | Normally stiff |

As a result, for Group I (control group), the meniscus defective parts were incompletely covered with thin layer of a fiber-like tissue even at 12 weeks after the operation, where the fibrocartilaginous tissue was only rarely regenerated.

On the other hand, for Group II (treatment group), all of the defects except one sample were covered with a thick layer of a fibrocartilage-like tissue at 3 and 6 weeks after the operation. A large number of cartilage-like cells and fibroblasts were observed in the fibrocartilage-like tissue, which were deeply stained with safranin-O and Toluidine blue stains. The defective parts were mostly filled with the fibrocartilage-like tissue at 12 weeks after the operation and a large number of cartilage-like cells were observed.

As can be appreciated from FIG. 2, gross observation scores for Group II were significantly higher than the scores for Group I at 3, 6 and 12 weeks after the operation (p=0.010, p=0.026 and p=0.020, respectively). Testing was performed by one-way analysis of variance (ANOVA) with Fischer's PSLD test for multiple comparison.

In addition, whether or not the meniscus defective parts, their surroundings and tips were ruptured at Weeks 3, 6 and 12 were also confirmed with the naked eyes. The results are shown in Table 3.

TABLE 3

| | Week 3 | Week 6 | Week 12 |
|---|---|---|---|
| Control group | 3/10 (30%) | 4/10 (40%) | 8/10 (80%) |
| Treatment group | 1/10 (10%) | 1/10 (10%) | 3/10 (30%) |

As can be appreciated from this table, whereas the incidence of rupture of the meniscus defective parts at Week 12 was as high as 80% for the control group, the incidence of rupture was minimized to 30% for the treatment group.

1-(5) Histological Evaluation

Histological evaluation was performed by staining the regenerated tissue with Hematoxylin and Eosin (HE), safranin-O and Toluidine blue according to a common method. In addition, they were scored according to "Criteria to Quantitatively Evaluate Histological Findings of Regenerated Tissues" shown in Table 2 of "The American Journal of Sports Medicine, (2010) Vol. 38 No. 4, p. 740-748". Specifically, each of the two criteria, namely, "number of chondrocytes" and "area of the cartilage tissue observed in the whole cross-sectional area" was evaluated in three scores of 0, 1 and 2, for comparison based on the total score. Score 2 is the best score. Specific evaluation criteria used for scoring are shown in the table below.

TABLE 4

|  | Score 0 | Score 1 | Score 2 |
| --- | --- | --- | --- |
| Number of chondrocytes | Almost no chondrocytes | Half the normal number | As many as the normal number |
| Area of the cartilage tissue observed in the whole cross-sectional area | Cartilage tissue rarely observed | Half as wide as that in the normal meniscus | As wide as that in the normal meniscus |

As a result, for Group I (control group), a synovial membrane-like tissue regenerated with many cells having round nuclei, at 3 weeks after the operation. The fibrous tissue slightly decreased, and the number of cells gradually decreased at 6 and 12 weeks after the operation (FIG. 3). For Group I, neither fibrocartilage-like cells nor matrix stained with safranin-O or Toluidine blue were observed.

On the other hand, for Group II (treatment group), the surface on the articular cavity side was covered with a relatively thick synovial membrane-like tissue at 3 weeks after the operation. The inner and outer normal tissues at the defective parts were connected via a loose connective tissue. At 3 weeks after the operation, fibrochondrocytes were observed with the remaining alginate gel. The matrix at the defective part was safranin-O positive. At 6 weeks after the operation, the alginate gel was gone and a homogeneous tissue having a shape of a meniscus was formed with a triangular cross section. In the homogeneous tissue, cells with relatively large round nuclei and cytoplasm-rich nuclei were distributed in a proteoglycan-rich tissue. The surface of the tissue was covered with a thin synovial membrane tissue.

At 12 weeks after the operation, large round cells which is cytoplasm-rich and has round or oval nuclei were distributed in the center of the defective meniscal tissue. The matrix surrounding these cells was positively stained with safranin-O and Toluidine blue stains.

For comparison, pictures of the stained meniscus tissue in a normal state are also shown. The pictures of the stained tissue of Group II (treatment group) show that the injured meniscus parts were repaired to an extent with almost no difference from the menisci in the normal state (FIG. 3).

The histological scores for Group II were significantly higher than those for Group I at 3 and 12 weeks after the operation (p=0.029 and p=0.016, respectively) (FIG. 3). Testing was performed by one-way analysis of variance (ANOVA) with Fischer's PSLD test for multiple comparison.

Meanwhile, for Group I, the histological scores at 12 weeks after the operation significantly decreased from the scores at 3 and 6 weeks after the operation.

1-(6) Evaluation of Mechanical Strength

The mechanical strength of the menisci was evaluated for four groups, namely, Group I (control group) and Group II (treatment group) at 6 weeks after the operation, Group II (treatment group) at 12 weeks after the operation and the normal group (n=6). Since the incidence of meniscus rupture for Group I (control group) reached 80% at 12 weeks after the operation, they were excluded from the evaluation.

The menisci of each group were frozen at −80° C. for a day or longer. The menisci thawed by spending a few hours were used for the experiment. Moisture was maintained with physiological saline during and after the thawing.

An autograph (Autograph AG-X series, Autograph test machine, AG-20kNX, SHIMADZU) was used to evaluate the stiffness of the repaired tissue. The meniscus was placed on the autograph, an indenter tip with a diameter of 0.50 mm was pressed against the repaired tissue for 0.5 mm at a rate of 0.1 mm/s and kept there for 30 seconds. This was repeated for five times at intervals of 240 seconds. The third, fourth and fifth repeats among the total of five repeats were used to measure the stiffness of each sample based on the slope (N/mm) of the load (N) and the depth (mm) upon pressing for 0.4-0.5 mm. The results are shown in FIGS. 4 and 5.

Significant difference was observed between the control group at Week 6 and the treatment group at Week 6 (P=0.006), and between the control group at Week 6 and the treatment group at Week 12 (P=0.015).

1-(7) Results

Thus, the fibrocartilage at a defective part was regenerated and also the mechanical strength was enhanced by filling the rabbit meniscus defects with the low endotoxin sodium alginate and gelling the low endotoxin sodium alginate with a calcium chloride solution.

To date, several methods have been proposed for treating a defective part of a meniscus, but it is known that it is not easy to regenerate the fibrocartilaginous tissue and also to recover the mechanical strength. This time the low endotoxin alginate gel surprisingly recovered the mechanical strength.

From the above-described results, the composition of the present invention was suggested to possibly promote a meniscus injury repair in an injured meniscus part, especially, in a defective part or a torn part and also in a sutured injured part. Moreover, since regeneration of a meniscus was confirmed for a defect (diameter 2 mm) that was relatively large regarding the size of the rabbit meniscus, the composition of the present invention was also suggested to be effective for the treatment of an injured part in the avascular area of the meniscus. Hence, the composition of the present invention was suggested to be effective, if necessary, in combination with suturing, for the treatment of a meniscus injury at an injured part in both vascular and avascular areas of the meniscus.

Example 2: Combinational Use with Meniscus Suturing

A tear caused in a meniscus of a target is subjected to a meniscus suturing operation according to a common method. While the meniscus suturing is not particularly limited, it may be performed, for example, by measuring the size of the torn part of the injured meniscus and arthroscopically suturing by inserting a suturing tool or the like in the knee joint. After suturing, the 2 w/w % low endotoxin sodium alginate solution used in Example 1 is applied to the sutured part. A 100 mM calcium chloride solution is added to that surface. After a few minutes, the affected site is washed with physiological saline. The opening made for inserting the arthroscope, the surgical instruments and else is closed by suturing.

After a predetermined period of time, the repair of the site treated by the combination of the suture and the sodium alginate solution is evaluated.

Example 3: Administration of Low Endotoxin Sodium Alginate to Sheep Meniscus Defect 3-(1) Preparation of Sheep Meniscus Defect (Punched Out) Models A columnar defect having a diameter of 4.0 mm was made through each of the anterior segments of the medial menisci on the avascular side in both knee joints of 5-7 month old sheep (Suffolk) with a punch instrument (BPP-40F with plunger system, Lot No. 16L08, Kai Industries), to obtain meniscus defect models.

The prepared meniscus defect models (n=20) were divided into two groups, where Group I received no treatment as an untreated group (n=10) whereas the defective parts of Group II were filled with a low endotoxin sodium alginate solution as a treatment group (n=10).

3-(2) Filling Low Endotoxin Sodium Alginate Solution

The sheep meniscus defects prepared in 3-(1) is sufficiently filled with the 2 w/w % low endotoxin sodium alginate solution prepared in 1-(1) of Example 1 while placing a plastic medicine spoon underneath. 2-5 ml of a 100 mM calcium chloride solution is added to the surface of the filled solution, kept for about a minute for gelation of the surface. Thereafter, the part applied with the calcium chloride solution is washed away with physiological saline (Group II: treatment group).

For both Groups I and II, the sheep are euthanatized at 3 weeks (n=2 each), 6 weeks (n=2 each), 12 weeks (n=4 each) and 24 weeks (n=2 each) after the operation to collect the menisci for gross evaluation and histological evaluation of the collected tissue specimens.

3-(3) Evaluation

In the gross evaluation, the shape, the color, the presence of gloss, the stiffness and the size are observed with the naked eyes.

For histological evaluation, stained specimens are prepared with Hematoxylin-Eosin (HE), safranin-O and Toluidine blue according to a common method for evaluation. For gross evaluation, evaluation is performed in the same manner as described in Example 1-(4) above by scoring according to "Criteria to Quantitatively Evaluate the Volume and Quality of Regenerated Tissues in Gross Observation" shown in Table 1 of "The American Journal of Sports Medicine, (2010) Vol. 38 No. 4, p. 740-748". For histological evaluation, evaluation is performed in the same manner as described Example 1-(5) above by scoring according to "Criteria to Quantitatively Evaluate Histological Findings of Regenerated Tissues" shown in Table 2 (ibid.). For immunohistological evaluation, immunostaining is performed with an anti-type I collagen stain, an anti-type II collagen stain, an anti-alginate and anti-α-SMA according to a common method for evaluation.

Group II (treatment group) and Group I (untreated group) are compared to evaluate the effect of the low endotoxin sodium alginate to regenerate the menisci.

The invention claimed is:

1. A method for treating a fibrocartilaginous tissue injury with a composition, comprising applying the composition to an injured fibrocartilaginous tissue part of a target, wherein the composition has fluidity or is flaky or powdery when applied to the injured fibrocartilaginous tissue part, and wherein the composition comprises a monovalent metal salt of alginic acid, wherein said applying results in regenerating of the injured fibrocartilaginous tissue part, wherein the fibrocartilaginous tissue part is a part of at least one selected from the group consisting of a meniscus, a triangular fibrocartilage, an articular disc and an annulus fibrosus of an intervertebral disc.

2. A method according to claim 1, wherein the monovalent metal salt of alginic acid is a low endotoxin monovalent metal salt of alginic acid.

3. The method according to claim 1, wherein applying the composition to the injured fibrocartilaginous tissue part comprises bringing the composition into contact with the injured fibrocartilaginous tissue part, and wherein the composition has fluidity when brought into contact with the injured fibrocartilaginous tissue part.

4. The method according to claim 1, wherein the composition having fluidity is at least partially cured after the application to the injured fibrocartilaginous tissue part.

5. The method according to claim 4, wherein the composition having fluidity is cured by bringing a crosslinking agent into contact with at least a part of the surface of the composition.

6. The method according to claim 1, wherein the apparent viscosity of the composition having fluidity is 100 mPa·s-30000 mPa·s as measured with a cone-plate viscometer (sensor: 35/1) under a condition wherein the measurement temperature is 20° C., the rotation speed is 0.5 rpm, and the reading time is 2.5 minutes of measurement to obtain an average value between 0.5 to 2.5 minutes after the start of the measurement.

7. The method according to claim 1, wherein the weight-average molecular weight (absolute molecular weight) of the monovalent metal salt of alginic acid is 30,000 or more as measured by a GPC-MALS method.

8. The method according to claim 1, wherein the concentration of the monovalent metal salt of alginic acid in the composition having fluidity is 0.1 w/w % to 5 w/w %.

9. The method according to claim 3, wherein the composition having fluidity does not contain a crosslinking agent in an amount that allows curing of the composition upon making contact with the injured fibrocartilaginous tissue part of the target.

10. The method according to claim 3, wherein the composition having fluidity is brought into contact with a crosslinking agent for curing the composition after applying the composition to the injured fibrocartilaginous tissue part of the target.

11. The method according to claim 1, wherein the composition having fluidity has fluidity that allows injection with a 21 G needle after leaving the composition to stand at 20° C. for an hour.

12. The method according to claim 5, wherein the crosslinking agent is a divalent or higher valent metal ion compound.

13. The method according to claim 1, wherein the fibrocartilaginous tissue injury is at least one condition or disease selected from the group consisting of a meniscus injury, a traumatic meniscus injury, a degenerative meniscus, a discoid meniscus, osteochondritis dissecans, cartilage degeneration, an intracapsular ligament injury, a sports injury, osteoarthritis and a triangular fibrocartilage complex injury and/or degeneration.

14. The method according to claim 1, wherein the injured fibrocartilaginous tissue part is a sutured injured fibrocartilaginous tissue part.

15. The method according to claim 1, wherein the composition is applied to the injured fibrocartilaginous tissue part in combination with suturing.

16. The method according to claim 1, wherein the composition is in a dry state or a solution state before being applied to the injured fibrocartilaginous tissue part.

17. The method according to claim 16, wherein the composition in a dry state is a lyophilizate.

18. The method according to claim 1 comprising the steps of:
(a) enabling visual recognition of the injured fibrocartilaginous tissue part through an incision or with an arthroscope or an endoscope;

(b) if necessary, removing an unnecessary tissue from the injured fibrocartilaginous tissue part and the peripheral part thereof;
(c) if necessary, suturing the injured fibrocartilaginous tissue part;
(d) applying the composition containing the monovalent metal salt of alginic acid to the injured fibrocartilaginous tissue part;
(e) if necessary, adding a crosslinking agent to the surface of the applied composition, and leaving the resultant for a predetermined period of time to bring the composition into contact with the crosslinking agent;
(f) if necessary, washing the site where the crosslinking agent had been added; and
(g) if necessary, closing the incision or the opening resulting from insertion of the arthroscope, the endoscope or other instrument.

19. The method according to claim 1, further comprising providing a kit comprising at least a monovalent metal salt of alginic acid and a crosslinking agent before applying the composition.

20. The method according to claim 1, wherein the composition does not contain a growth factor and is free of cells.

* * * * *